US010751124B2

(12) United States Patent
Eisenfrats et al.

(10) Patent No.: US 10,751,124 B2
(45) Date of Patent: Aug. 25, 2020

(54) METHODS FOR IMPLANTING AND REVERSING STIMULI-RESPONSIVE IMPLANTS

(71) Applicant: Contraline, Inc., Charlottesville, VA (US)

(72) Inventors: Kevin Eisenfrats, Charlottesville, VA (US); Gregory Grover, Charlottesville, VA (US); Eric Moran, Charlottesville, VA (US)

(73) Assignee: Contraline, Inc., Charlottesville, VA (US)

( * ) Notice: Subject to any disclaimer, the term of this patent is extended or adjusted under 35 U.S.C. 154(b) by 0 days.

(21) Appl. No.: 15/863,759

(22) Filed: Jan. 5, 2018

(65) Prior Publication Data

US 2018/0185096 A1   Jul. 5, 2018

Related U.S. Application Data

(60) Provisional application No. 62/442,583, filed on Jan. 5, 2017, provisional application No. 62/566,592, filed on Oct. 2, 2017.

(51) Int. Cl.
*A61F 6/20* (2006.01)
*A61B 18/24* (2006.01)
(Continued)

(52) U.S. Cl.
CPC ............ *A61B 18/245* (2013.01); *A61B 8/481* (2013.01); *A61B 17/1219* (2013.01);
(Continued)

(58) Field of Classification Search
CPC ................ A61B 8/481; A61B 19/5244; A61B 2019/5272; A61B 19/52;
(Continued)

(56) References Cited

U.S. PATENT DOCUMENTS 3,223,083 A   12/1965   Cobey
3,716,056 A   2/1973   Brodsky et al.
(Continued)

FOREIGN PATENT DOCUMENTS

CN   101812194 B   4/2012
CN   203493942 U   3/2014
(Continued)

OTHER PUBLICATIONS

Naughton, C. K., et al., "The Use of URYX for Reversible Vasectomy in a Rabbit Model", Journal of Andrology, 25: 545-553 (2004).
(Continued)

*Primary Examiner* — Ophelia A Hawthorne
(74) *Attorney, Agent, or Firm* — New River Valley IP Law, P.C.; Michele L. Mayberry

(57) ABSTRACT

Described are methods for reversible occlusion of a body lumen by way of degradation as a result of exposure to one or more stimuli such as light. The methods include administering one or more substance(s) into a body lumen of a subject and forming a stimuli-responsive polymer mass in the body lumen from the one or more substance(s). The mass is sufficient to occlude the body lumen in a manner that prevents transport of at least one material through the body lumen and is susceptible to on-command reversal in the body lumen upon exposure to one or more stimuli. The methods include administering one or more stimuli to a polymer mass in a body lumen for a time and intensity to cause the reverse the polymer mass. The methods are particular useful for applications in which it is desirable to temporarily occlude a body lumen, such as male and female contraception.

17 Claims, 10 Drawing Sheets

(51) Int. Cl.

| | | |
|---|---|---|
| *A61F 6/22* | (2006.01) | |
| *A61B 8/08* | (2006.01) | |
| *A61N 5/06* | (2006.01) | |
| *A61B 17/12* | (2006.01) | |
| *A61B 17/32* | (2006.01) | |
| *A61N 7/02* | (2006.01) | |
| *A61K 41/00* | (2020.01) | |
| *A61L 27/50* | (2006.01) | |
| *A61L 31/14* | (2006.01) | |
| *A61K 49/22* | (2006.01) | |
| *A61L 27/54* | (2006.01) | |
| *A61B 17/34* | (2006.01) | |
| *A61B 18/00* | (2006.01) | |
| *A61B 90/00* | (2016.01) | |
| *A61B 17/00* | (2006.01) | |
| *A61B 7/00* | (2006.01) | |

(52) U.S. Cl.
CPC .. *A61B 17/12109* (2013.01); *A61B 17/12186* (2013.01); *A61B 17/320068* (2013.01); *A61F 6/22* (2013.01); *A61K 41/0028* (2013.01); *A61L 27/50* (2013.01); *A61L 31/14* (2013.01); *A61N 5/062* (2013.01); *A61N 7/022* (2013.01); *A61B 7/00* (2013.01); *A61B 8/085* (2013.01); *A61B 8/0833* (2013.01); *A61B 8/483* (2013.01); *A61B 8/486* (2013.01); *A61B 17/3403* (2013.01); *A61B 2017/00898* (2013.01); *A61B 2018/00416* (2013.01); *A61B 2018/00547* (2013.01); *A61B 2018/00559* (2013.01); *A61B 2018/00982* (2013.01); *A61B 2090/376* (2016.02); *A61F 6/206* (2013.01); *A61K 49/223* (2013.01); *A61K 49/226* (2013.01); *A61L 27/54* (2013.01); *A61L 2430/36* (2013.01)

(58) Field of Classification Search
CPC ...... A61B 2019/5251; A61B 17/12022; A61B 17/12099; A61L 2430/36; A61F 6/225; A61F 6/22; A61F 6/206; A61F 6/20
See application file for complete search history.

(56) References Cited

U.S. PATENT DOCUMENTS

| | | |
|---|---|---|
| 4,044,757 A | 8/1977 | McWhorter et al. |
| 4,269,174 A | 5/1981 | Adair |
| 4,273,109 A | 6/1981 | Enderby |
| 4,804,691 A | 2/1989 | English et al. |
| 4,887,605 A | 12/1989 | Angelsen et al. |
| 4,920,982 A | 5/1990 | Goldstein |
| 4,967,949 A | 11/1990 | Sandhaus |
| 4,978,336 A | 12/1990 | Capozzi et al. |
| 4,979,942 A | 12/1990 | Wolf et al. |
| 5,065,751 A | 11/1991 | Wolf |
| 5,240,997 A | 8/1993 | Yanai et al. |
| 5,248,311 A | 9/1993 | Black et al. |
| 5,258,042 A | 11/1993 | Mehta |
| 5,380,317 A | 1/1995 | Everett et al. |
| 5,383,896 A | 1/1995 | Gershony et al. |
| 5,437,660 A | 8/1995 | Johnson et al. |
| 5,488,075 A * | 1/1996 | Guha .................. A61K 31/765 522/168 |
| 5,575,815 A | 11/1996 | Slepian et al. |
| 5,607,419 A | 3/1997 | Amplatz et al. |
| 5,612,052 A | 3/1997 | Shalaby |
| 5,667,767 A | 9/1997 | Greff et al. |
| 5,695,740 A | 12/1997 | Porter |
| 5,702,717 A | 12/1997 | Cha et al. |
| 5,714,159 A | 2/1998 | Shalaby |
| 5,749,968 A | 5/1998 | Melanson et al. |
| 5,797,397 A | 8/1998 | Rosenberg |
| 5,833,682 A | 11/1998 | Amplatz et al. |
| 5,866,554 A | 2/1999 | Shalaby et al. |
| 5,947,893 A * | 9/1999 | Agrawal ............. A61F 2/30767 600/36 |
| 5,968,018 A | 10/1999 | Freeman et al. |
| 5,989,580 A | 11/1999 | Wallace et al. |
| 6,037,331 A | 3/2000 | Shalaby et al. |
| 6,066,325 A | 5/2000 | Wallace et al. |
| 6,096,052 A | 8/2000 | Callister et al. |
| 6,103,254 A | 8/2000 | Wallace et al. |
| 6,197,940 B1 | 3/2001 | Klinefelter |
| 6,224,893 B1 * | 5/2001 | Langer ................ A61K 9/0019 424/423 |
| 6,297,337 B1 | 10/2001 | Marchant et al. |
| 6,328,229 B1 | 12/2001 | Duronio et al. |
| 6,378,524 B1 | 4/2002 | Jones |
| 6,379,373 B1 | 4/2002 | Sawhney et al. |
| 6,394,314 B1 | 5/2002 | Sawhney et al. |
| 6,413,539 B1 | 7/2002 | Shalaby |
| 6,432,116 B1 | 8/2002 | Callister et al. |
| 6,454,762 B1 | 9/2002 | Roesler et al. |
| 6,461,325 B1 | 10/2002 | Delmotte et al. |
| 6,461,569 B1 | 10/2002 | Boudreaux |
| 6,464,663 B1 | 10/2002 | Zinger |
| 6,485,426 B2 | 11/2002 | Sandhu |
| 6,514,534 B1 | 2/2003 | Sawhney |
| 6,514,535 B2 | 2/2003 | Marchant |
| 6,531,111 B1 | 3/2003 | Thomas et al. |
| 6,610,033 B1 | 8/2003 | Melanson et al. |
| 6,660,247 B1 | 12/2003 | Gutowska et al. |
| 6,703,047 B2 | 3/2004 | Sawhney et al. |
| 6,719,778 B1 | 4/2004 | Tassel et al. |
| 6,723,090 B2 | 4/2004 | Altshuler et al. |
| 6,723,781 B1 | 4/2004 | Frate et al. |
| 6,756,031 B2 | 6/2004 | Evans et al. |
| 6,802,838 B2 | 10/2004 | Loeb et al. |
| 6,852,099 B2 | 2/2005 | Redl et al. |
| 6,858,219 B2 | 2/2005 | Evans et al. |
| 6,957,747 B2 | 10/2005 | Peeler et al. |
| 6,970,587 B1 | 11/2005 | Rogers |
| 7,022,073 B2 | 4/2006 | Fan et al. |
| 7,073,504 B2 | 7/2006 | Callister et al. |
| 7,135,027 B2 | 11/2006 | Delmotte |
| 7,160,931 B2 | 1/2007 | Cheng et al. |
| 7,252,677 B2 | 8/2007 | Burwell et al. |
| 7,347,850 B2 | 3/2008 | Sawhney |
| 7,396,354 B2 | 7/2008 | Rychnovsky et al. |
| 7,398,780 B2 | 7/2008 | Callister et al. |
| 7,641,075 B2 | 1/2010 | Crews |
| 7,694,683 B2 | 4/2010 | Callister et al. |
| 7,754,212 B2 | 7/2010 | Klinefelter |
| 7,789,891 B2 | 9/2010 | Wallace |
| 7,871,637 B2 | 1/2011 | Qian et al. |
| 7,914,514 B2 | 3/2011 | Calderon |
| 7,914,541 B2 | 3/2011 | Sawhney et al. |
| 7,918,863 B2 | 4/2011 | Nguyen et al. |
| 7,975,697 B2 | 7/2011 | Callister et al. |
| 8,048,086 B2 | 11/2011 | Lee-Sepsick et al. |
| 8,048,101 B2 | 11/2011 | Lee-Sepsick et al. |
| 8,052,669 B2 * | 11/2011 | Lee-Sepsick ....... A61M 31/005 424/1.11 |
| 8,113,205 B2 | 2/2012 | Callister et al. |
| 8,123,693 B2 | 2/2012 | Connor et al. |
| 8,226,680 B2 | 7/2012 | Wallace |
| 8,235,047 B2 | 8/2012 | Swann et al. |
| 8,257,723 B2 | 9/2012 | Noyes |
| 8,303,981 B2 | 11/2012 | Wallace et al. |
| 8,316,853 B2 | 11/2012 | Lee-Sepsick et al. |
| 8,316,854 B2 | 11/2012 | Lee-Sepsick et al. |
| 8,322,341 B2 | 12/2012 | Koeller |
| 8,324,193 B2 | 12/2012 | Lee-Sepsick et al. |
| 8,336,552 B2 | 12/2012 | Lee-Sepsick et al. |
| 8,343,183 B2 | 1/2013 | D'Alessio et al. |
| 8,343,710 B1 | 1/2013 | Anseth et al. |
| 8,353,892 B2 | 1/2013 | Thompson et al. |
| 8,357,378 B2 | 1/2013 | Wallace et al. |
| 8,360,064 B2 | 1/2013 | Swann et al. |
| 8,434,489 B2 | 5/2013 | Gopal et al. |

(56) References Cited

U.S. PATENT DOCUMENTS

| | | |
|---|---|---|
| 8,440,487 B2 | 5/2013 | Furumura |
| 8,512,729 B2 | 8/2013 | Wallace et al. |
| 8,523,848 B2 | 9/2013 | Fried et al. |
| 8,550,085 B2 | 10/2013 | Callister et al. |
| 8,551,001 B2 | 10/2013 | Connor et al. |
| 8,603,025 B2 | 12/2013 | Pongratz et al. |
| 8,603,080 B1 | 12/2013 | Fried et al. |
| 8,603,511 B2 | 12/2013 | Wallace et al. |
| 8,613,282 B2 | 12/2013 | Nikolchev et al. |
| 8,689,792 B2 | 4/2014 | Mujwid et al. |
| 8,695,606 B2 | 4/2014 | Lee-Sepsick et al. |
| 8,726,906 B2 | 5/2014 | Lee-Sepsick et al. |
| 8,766,853 B2 | 7/2014 | Furumura et al. |
| 8,801,764 B2 | 8/2014 | Suarez et al. |
| 8,933,784 B2 | 1/2015 | Furumura et al. |
| 8,960,501 B2 | 2/2015 | Pappalardo |
| 8,986,730 B2 | 3/2015 | Sawhney et al. |
| 9,034,053 B2 | 5/2015 | Lee-Sepsick et al. |
| 9,155,543 B2 | 10/2015 | Walsh et al. |
| 9,180,196 B2 | 11/2015 | Anseth et al. |
| 9,193,816 B2 | 11/2015 | Jiang et al. |
| 9,220,880 B2 | 12/2015 | Lee-Sepsick et al. |
| 9,308,283 B2 | 4/2016 | Campbell et al. |
| 9,445,795 B2 | 9/2016 | Ohri et al. |
| 9,463,004 B2 | 10/2016 | Campbell et al. |
| 9,586,005 B2 | 3/2017 | Steffen |
| 9,707,319 B2 | 7/2017 | Geppert et al. |
| 9,750,695 B2 | 9/2017 | Richard |
| 9,861,515 B2 | 1/2018 | DePinto et al. |
| 10,155,063 B2 | 12/2018 | Herr et al. |
| 2002/0051750 A1 | 5/2002 | Schutt et al. |
| 2002/0106328 A1 | 8/2002 | Johnson et al. |
| 2002/0106411 A1 | 8/2002 | Wironen et al. |
| 2002/0173586 A1 | 11/2002 | Jeong et al. |
| 2003/0185758 A1 | 10/2003 | Evans et al. |
| 2003/0199865 A1 | 10/2003 | Knudson et al. |
| 2003/0206864 A1 | 11/2003 | Mangin |
| 2004/0013292 A1 | 1/2004 | Raunig |
| 2004/0062808 A1 | 4/2004 | Langrana et al. |
| 2004/0087930 A1 | 5/2004 | Whalen et al. |
| 2004/0240715 A1 | 12/2004 | Wicker et al. |
| 2005/0045183 A1 | 3/2005 | Callister et al. |
| 2005/0147599 A1 | 7/2005 | Hunter et al. |
| 2005/0149117 A1* | 7/2005 | Khosravi ......... A61B 17/00491 |
| | | 606/215 |
| 2005/0192616 A1 | 9/2005 | Callister et al. |
| 2005/0266086 A1 | 12/2005 | Sawhney |
| 2005/0283098 A1 | 12/2005 | Conston et al. |
| 2006/0121087 A1 | 6/2006 | Williams et al. |
| 2006/0222596 A1 | 10/2006 | Askari et al. |
| 2006/0241452 A1 | 10/2006 | Cerofolini |
| 2007/0060906 A1 | 3/2007 | Wu |
| 2007/0163601 A1 | 7/2007 | Pollock et al. |
| 2007/0231366 A1 | 10/2007 | Sawhney et al. |
| 2008/0039890 A1 | 2/2008 | Matson et al. |
| 2008/0045865 A1 | 2/2008 | Kislev |
| 2008/0154345 A1 | 6/2008 | Taylor |
| 2008/0308110 A1 | 12/2008 | Callister et al. |
| 2009/0024155 A1 | 1/2009 | Lee-Sepsick et al. |
| 2009/0048588 A1 | 2/2009 | Peng et al. |
| 2009/0053276 A1 | 2/2009 | Richard |
| 2009/0076459 A1 | 3/2009 | Goldberg |
| 2009/0274678 A1 | 11/2009 | Calabro et al. |
| 2009/0277457 A1 | 11/2009 | Hoey et al. |
| 2010/0003297 A1 | 1/2010 | Tobias et al. |
| 2010/0006339 A1 | 1/2010 | Desai |
| 2010/0063392 A1 | 3/2010 | Nishina et al. |
| 2010/0068153 A1 | 3/2010 | Bangera et al. |
| 2010/0089406 A1 | 4/2010 | Kachiguina |
| 2010/0158813 A1 | 6/2010 | Paradossi et al. |
| 2010/0272672 A1 | 10/2010 | Kita et al. |
| 2010/0318035 A1 | 12/2010 | Edwards et al. |
| 2011/0021970 A1 | 1/2011 | Vo-Dinh et al. |
| 2011/0065809 A1 | 3/2011 | Benz et al. |
| 2011/0137150 A1 | 6/2011 | Connor et al. |
| 2011/0165114 A1* | 7/2011 | McCoy ............... A61K 9/0024 |
| | | 424/78.24 |
| 2012/0014978 A1 | 1/2012 | Hafner et al. |
| 2012/0149781 A1 | 6/2012 | Lee et al. |
| 2012/0165804 A1 | 6/2012 | Newell et al. |
| 2012/0192872 A1 | 8/2012 | Rudakov et al. |
| 2012/0226226 A1 | 9/2012 | Edwards et al. |
| 2012/0295214 A1 | 11/2012 | Wang et al. |
| 2013/0018314 A1 | 1/2013 | Teague et al. |
| 2013/0131632 A1 | 5/2013 | Mudd et al. |
| 2013/0230496 A1 | 9/2013 | Mohapatra et al. |
| 2013/0245604 A1 | 9/2013 | Kouyoumjian et al. |
| 2013/0331770 A1 | 12/2013 | Kirk et al. |
| 2013/0331771 A1 | 12/2013 | Kirk et al. |
| 2014/0046182 A1 | 2/2014 | Connor et al. |
| 2014/0114261 A1 | 4/2014 | Geppert et al. |
| 2014/0121699 A1 | 5/2014 | Anderson et al. |
| 2014/0128497 A1 | 5/2014 | Ladet et al. |
| 2014/0256831 A1 | 9/2014 | Ito et al. |
| 2014/0261446 A1 | 9/2014 | Sjoquist et al. |
| 2014/0276384 A1 | 9/2014 | Schwab et al. |
| 2015/0068531 A1 | 3/2015 | Lee-Sepsick et al. |
| 2015/0136144 A1 | 5/2015 | DePinto et al. |
| 2015/0231246 A1 | 8/2015 | Tae et al. |
| 2016/0024326 A1 | 1/2016 | Khan et al. |
| 2016/0114046 A1 | 4/2016 | Brudno et al. |
| 2016/0151535 A1 | 6/2016 | Hoare et al. |
| 2016/0153999 A1* | 6/2016 | Tibbitt ............... A61K 41/0028 |
| | | 435/7.23 |
| 2016/0193392 A1 | 7/2016 | Askari et al. |
| 2017/0014569 A1 | 1/2017 | Flanagan et al. |
| 2017/0136143 A1 | 5/2017 | Herr et al. |
| 2017/0136144 A1 | 5/2017 | Herr et al. |
| 2017/0189581 A1 | 7/2017 | Desai et al. |
| 2017/0296749 A1 | 10/2017 | Porcher |
| 2018/0028715 A1 | 2/2018 | Eisenfrats |
| 2018/0092769 A1 | 4/2018 | Depinto et al. |
| 2019/0038454 A1 | 2/2019 | Eisenfrats et al. |
| 2019/0053790 A1 | 2/2019 | Grover et al. |
| 2019/0060513 A1 | 2/2019 | Herr et al. |
| 2020/0147301 A1 | 5/2020 | Grover et al. |

FOREIGN PATENT DOCUMENTS

| | | |
|---|---|---|
| CN | 103724638 B | 12/2015 |
| EP | 0547530 A1 | 6/1993 |
| EP | 2233160 A2 | 9/2010 |
| EP | 3275469 A1 | 1/2018 |
| WO | 2009137446 A2 | 11/2009 |
| WO | 2009137446 A3 | 2/2010 |
| WO | 2008115694 A3 | 6/2010 |
| WO | 2012112417 A2 | 8/2012 |
| WO | 2015168090 A1 | 11/2015 |
| WO | 2016094535 A1 | 6/2016 |
| WO | 2016154288 A1 | 9/2016 |
| WO | 2016164828 A1 | 10/2016 |
| WO | 2017044983 A1 | 3/2017 |
| WO | 2017083753 A1 | 5/2017 |
| WO | 2017114908 A1 | 7/2017 |
| WO | 2017174071 A1 | 10/2017 |
| WO | 2018104537 A1 | 6/2018 |
| WO | 2018129369 A1 | 7/2018 |
| WO | 2019070632 A1 | 4/2019 |
| WO | 2020102234 A1 | 5/2020 |

OTHER PUBLICATIONS

Reddy, N. M., et al., "Vasectomy-Related Changes on Sonographic Examination of the Scrotum", J. Clin. Ultrasound, 32: 394-398 (2004).

Robinette, W.B. "Ultrasound Contrast Agents", JDMS 13:29S-34S, (1997).

Roy, S. et al.,"Polyelectrolyte polymer properties in relation to male contraceptive RISUG® action", Colloids and Surfaces B: Biointerfaces 69: 77-84 (2009).

Singh, Sunilk et al., "Amine-Modified Graphene: Thrombo-Protective Safer Alternative to Graphene Oxide for Biomedical

(56) References Cited

OTHER PUBLICATIONS

Applications," Jan. 1, 2012, vol. 6, No. 3, ACS NANO, pp. 3721-2740, XP055417936.

Soebadi, D. M., "Intravasal injection of formed-in-place medical grade silicone for vas occlusion", International Journal of Andrology, 18: 45-52 (1995).

T.L. Szabo et al., "Ultrasound Transducer Selection in Clinical Imaging Practice", Journal of Ultrasound in Medicine, 2013, 32(4):573-582.

Waller et al., "Azoospermia in rabbits following an intravas injection of Vasalgel", Basic and Clinical Andrology, 26:6(2016).

Zambon, J.V., "Efficacy of percutaneous vas occlusion compared with conventional vasectomy", BJU International, 86, 699-706 (2000).

Zhao, S.C., "Intravasal injection of formed-in-place silcone rubber as a method of vas occlusion", International Journal of Andrology, 15:460-464 (1992).

Zhao, S.C., Contraception, "Vas Deferens Occlusion by Percutaneous Injection of Polyurethane Elastomer Plugs: Clinical Experience and Reversibility", 41(5):453-459 (1990).

Co-pending U.S. Appl. No. 15/349,824, Response to Feb. 7, 2018 Non-Final Office Action dated May 7, 2018, 14 pages.

Co-pending International Application PCT/US2016/061671 International Preliminary Report on Patentability, dated May 24, 2018, 26 pages.

Co-pending International Application PCT/US2018/012654 (WO/2017/083753), International Search Report and Written Opinion, dated Mar. 26, 2018, 22 pages.

Co-pending U.S. Appl. No. 15/653,618, Non-Final Office Action dated May 31, 2018, 7 pages.

"Plug, socket & voltage by country". World Standards. At least as early as Oct. 2, 2017. http://www.worldstandards.eu/electricity/plug-voltage-by-country/.

"Silica Fibers". RP Photonics Encyclopedia. At least as early as Oct. 2, 2017. https://www.rp-photonics.com/silica_fibers.html.

"Syringe Needle Gauge Chart". Sigma Aldrich. At least as early as Oct. 2, 2017. http://www.sigmaaldrich.com/chemistry/stockroom-reagents/learning-center/technicallibrary/needle-gauge-chart.html.

414093 Sigma-Aldrich Product Safety Data Sheet ("poly(vinyl alcohol coethylene) with ethylene 32 mol %"). Version 4.2. Revision Date: Jun. 25, 2014. Print Date: Mar. 27, 2017.

Abdala, N. et al., "Use of Ethylene Vinyl Alcohol Copolymer for Tubal Sterilization by Selective Catheterization in Rabbits", Journal of Vascular and Interventional Radiology, 12(8): 979-984 (2001).

Attaran, R. R, "Protocol for Optimal Detection and Exclusion of a Patent Foramen Ovale Using Transthoracic Echocardiography with Agitated Saline Microbubbles" (2006), Echocardiography (Mount Kisco, N.Y.), 23(7), 616-22.

Bank et al., "Contribution of Collagen, Elastin, and Smooth Muscle to In Vivo Human Brachial Artery Wall Stress and Elastic Modulus", Circulation. 1996;94:3263-3270.

Calliada F, et al., "Ultrasound contrast agents: basic principles", Eur J Radio!. 1998 27 Suppl 2:S157-60.

Chaki, S.P. et al., "A short-term evaluation of semen and accessory sex gland function in phase III trial subjects receiving intravasal contraceptive RISUG", Contraception, 67(1):73-78 (2003).

Clenney TL, "Vasectomy Techniques," Am Fam Physician. 1999; 60(1):137-146.

Co-pending U.S. Appl. No. 15/349,824, Final Office Action dated Aug. 2, 2017, 17 pages.

Co-pending U.S. Appl. No. 15/349,824, Interview Summary, dated Dec. 13, 2017, 3 pages.

Co-pending U.S. Appl. No. 15/349,824, Non-Final Office Action dated Jan. 26, 2017, 12 pages.

Co-pending U.S. Appl. No. 15/349,824, Non-Final Office Action dated Feb. 7, 2018, 13 pages.

Co-pending U.S. Appl. No. 15/349,824, published as US 20170136143 on May 18, 2017.

Co-pending U.S. Appl. No. 15/349,824, RCE filed in response to Aug. 2, 2017 Final Office Action, dated Oct. 6, 2017, 18 pages.

Co-pending U.S. Appl. No. 15/349,824, Response to Jan. 26, 2017 Non-Final Office Action dated Apr. 26, 2017, 17 pages.

Co-pending U.S. Appl. No. 15/349,824, Supplemental Amendment, dated Dec. 27, 2017, 10 pages.

Co-pending European Patent Application No. 17183620.8, Extended European Search Report dated Nov. 6, 2017, 8 pages.

Co-pending European Patent Application No. 17183620.8, filed Jul. 27, 2017, published as EP3275469 on Jan. 31, 2018.

Co-pending International Application No. PCT/US18/12654, filed Jan. 5, 2018.

Co-pending International Application PCT/US2016/061671 filed Nov. 11, 2016, published as WO/2017/083753 on May 18, 2017.

Co-pending U.S. Appl. No. 15/349,806, filed Nov. 11, 2016, published as US 20170136144 on May 18, 2017.

Co-pending U.S. Appl. No. 15/349,806, Non-Final Office Action dated Aug. 22, 2017, 14 pages.

Co-pending U.S. Appl. No. 15/349,806, Non-Final Office Action dated Feb. 24, 2017, 9 pages.

Co-pending U.S. Appl. No. 15/349,806, Response to Feb. 24, 2017 Non-Final Office Action dated May 23, 2017,14 pages.

Co-pending U.S. Appl. No. 15/653,618 filed Jul. 19, 2017, published as US 20180028715 on Feb. 1, 2018.

Co-pending U.S. Appl. No. 15/653,618, Response to Restriction Requirement dated Jan. 8, 2018, filed Mar. 8, 2018, 8 pages.

Co-pending U.S. Appl. No. 15/653,618, Restriction Requirement dated Jan. 8, 2018, 9 pages.

Cosgrove D, "Ultrasound contrast agents: An overview", Radiology 2006 vol. 60, Issue 3, pp. 324-330.

El-Sherif, D. M., & Wheatley, M. A. "Development of a novel method for synthesis of a polymeric ultrasound contrast agent", Journal of Biomedical Materials Research Part A, (2003) 66A(2), 347-355.

Fan, H., Wang, L., Zhao, K., Li, N., Shi, Z., Ge, Z., & Jin, Z. (2010). Fabrication, mechanical properties, and biocompatibility of graphene-reinforced chitosan composites. Biomacromolecules, 11(9), 2345-2351.

Flickinger CJ, et al. The influence of vasovasostomy on testicular alterations after vasectomy in lewis rats. Anat Rec, 1987. 217(2): 137-145.

Flickinger CJ. Alterations in the fine structure of the rat epididymis after vasectomy. Anat Rec, 1972. 173(3): 377-300.

Flickinger CJ. Ultrastructure of the rat testis after vasectomy. Anat Rec, 1972. 174(4): 477-493.

Guha, S.K. et al., "Phase II Clinical Trial of a Vas Deferens Injectable Contraceptive for the Male Contraception", 56:4, 245-250 (1997).

Hashemi, E., Akhavan, O., Shamsara, M., Rahighi, R., Esfandiar, A., & Tayefeh, A.R. (2014). Cyto and genotoxicities of graphene oxide and reduced graphene oxide sheets on spermatozoa. RSC Advances, 4(52), 27213-27223.

International Application PCT/US2016/061671 filed Nov. 11, 2016, International Search Report and Written Opinion dated Mar. 17, 2017, 29 pages.

International Application PCT/US2016/061671 filed Nov. 11, 2016, Invitation to Pay Additional Fees and Partial Search Report dated Jan. 10, 2017, 2 pages.

J. Zhou et al. "Optical Fiber Tips and Their Applications". Polymicro Technologies. Nov. 2007. https://www.molex.com/mx_upload/superfamily/polymicro/pdfs/Optical_Fiber_Tips_and_Their_Applications_Nov_2007_pdf.

Jha, R.K., et al., "Smart RISUG: A potential new contraceptive and its magnetic field-mediated sperm interaction", International Journal of Nanomedicine, 4:55-64 (2009).

Koul, V. et al., "Reversibility With Sodium Bicarbonate of Styrene Maleic Anhydride, an Intravasal Injectable Contraceptive, in Male Rats", Contraception 58(4):227-31 (1998).

Lahiri, D., Dua, R., Zhang, C., de Socarraz-Novoa, I., Bhat, A., Ramaswamy, S., & Agarwal, A. (2012). Graphene nanoplatelet-induced strengthening of ultrahigh molecular weight polyethylene and biocompatibility in vitro. ACS applied materials & interfaces, 4(4), 2234-2241.

(56) References Cited

OTHER PUBLICATIONS

Lee W. C., Lim, C. H. Y., Shi, H., Tang, L.A., Wang, Y., Lim, C. T., & Loh, K. P. (2011). Origin of enhanced stem cell growth and differentiation on graphene and graphene oxide. ACS nano, 5(9), 7334-7341.
Liu, X. et al., "The Relationship Between the Vas Volume and the Anatomic Size of the Vas Deferens", Contraception, 56(6): 391-394 (1997).
Lohiya, N.K. et al., "Preclinical evaluation for noninvasive reversal following long-term vas occlusion with styrene maleic anhydride in langur monkeys", Contraception, 71(3):214-226 (2005).
Lohiya N.K. et al., "RISUG: An intravasal injectable male contraceptive", Indian J Med Res 140 (Supplement): 63-72 (2014).
McKay, Craig S., et al., "Click Chemistry in Complex Mixtures: Bioorthogonal Bioconjugation", Chem Biol. Sep. 18, 2014; 21(9): 1075-1101. doi:10.1016/J.chembiol.2014.09.002., (2014), 51 pgs.
Mehrali, M., Moghaddam, E., Shirazi, S. F. S., Baradaran, S., Mehrali, M., Latibari, S. T. & Osman, N. A. A. (2014). Mechanical and in vitro biological performance of graphene nanoplatelets reinforced calcium silicate composite. PloS one, 9(9), e106802.
Middleton, W.D., et al., "High-Resolution Sonography of the Normal Extrapelvic Vas Deferens", J Ultrasound Med., 28(7):839-46 (2009).
A. Kloxin et al., "Photodegradable hydrogels for dynamic tuning of physical and chemical properties", Science. Apr. 3, 2009; 324(5923): 59-63.
Akram F, Kim JH, Lee C-G, Choi KN. Segmentation of Regions of Interest Using Active Contours with SPF Function. Comput Math Methods Med. 2015; 2015:e710326.
Co-pending U.S. Appl. No. 15/349,824, Notice of Allowance dated Aug. 15, 2018, 10 pages.
Co-pending Australian Patent Application, published as AU2016353345 on Jun. 14, 2018 (see WO2017083753).
Co-pending Canada Patent Application, published as CA3004745 on May 18, 2017 (see WO2017083753).
Co-pending European Patent Application No. 16865154.5, filed May 23, 2018, published as EP3383870 on Sep. 19, 2018, amended claims, (see WO2017083753).
Co-pending European Patent Application No. 17183620.8, Response to Extended European Search Report dated Jul. 31, 2018, 16 pages.
Co-pending International Application No. PCT/US18/53853, filed Oct. 2, 2018.
Co-pending International Application No. PCT/US18/53853, Search Report and Written Opinion, dated Dec. 13, 2018, 16 pages.
Co-pending U.S. Appl. No. 16/173,539, filed Oct. 29, 2018.
Co-pending U.S. Appl. No. 15/653,618, Final Office Action dated Nov. 19, 2018, 7 pages.
Co-pending U.S. Appl. No. 15/653,618, Response to May 31, 2018 Non-Final Office Action dated Aug. 31, 2018, 9 pages.
Co-pending U.S. Appl. No. 15/653,618, Response to Nov. 19, 2018 Final Office Action dated Feb. 19, 2018, 10 pages.
Co-pending U.S. Appl. No. 16/104,701, filed Aug. 17, 2018.
Co-pending U.S. Appl. No. 16/156,947, filed Oct. 10, 2018.
David A. Fulton, "Synthesis: Click chemistry gets reversible" Nature Chemistry 8, 899-900 (2016.).
Emilie Dressaire, Rodney Bee, David C. Bell, Alex Lips, Howard A. Stone. "Interfacial Polygonal Nanopatterning of Stable Microbubbles". Science May 30, 2008: vol. 320, Issue 5880, pp. 1198-1201.
Garmiak, R., & Shah, P. M. (1968). Echocardiography of the aortic root. Invest Radiology, 3, 356-366.
Hafez, ES, et al. "Atlas of Human Reproduction: by Scanning Electron Microscopy", 1982, MTP Press, Hingham, MA. Part 1-1 (separated into 4 parts for Filing), 85 pgs.
Hafez, ES, et al. "Atlas of Human Reproduction: By Scanning Electron Microscopy", 1982, MTP Press, Hingham, MA. Part 1-2 (separated into 4 parts for Filing), 85 pgs.
Hafez, ES, et al. "Atlas of Human Reproduction: By Scanning Electron Microscopy", 1982, MTP Press, Hingham, MA. Part 2-1 (separated into 4 parts for Filing), 66 pgs.
Hafez, ES, et al. "Atlas of Human Reproduction: by Scanning Electron Microscopy", 1982, MTP Press, Hingham, MA. Part 2-2 (separated into 4 parts for Filing), 101 pgs.
Lu An, He Hu, Jing Du, Jie Wei, Li Wang, Hong Yang, Dongmei Wu, Haili Shi, Fenghua Li, Shiping Yang, Paramagnetic hollow silica nanospheres for in vivo targeted ultrasound and magnetic resonance imaging, Biomaterials, vol. 35, Issue 20, 2014, pp. 5381-5392.
Mayans, D.; Cartwright, MS.; Walker, F.O. Neuromuscular ultrasonography: Quantifying muscle and nerve measurements. Phys. Med. Rehabil. Clin. N. Am. 2011, 23, 133-148.
Noble JA, Boukerroui D. Ultrasound image segmentation: a survey. IEEE Trans Med Imaging. Aug. 2006; 25(8):987-1010.
Paefgen V, Doleschel D, Kiessling F. Evolution of contrast agents for ultrasound imaging and ultrasound-mediated drug delivery. Frontiers in Pharmacology. 2015;6:197. doi:10.3389/fphar.2015. 00197.
Stockton DM et al. "No-scalpel vasectomy: a technique for family physicians." Am Fam Physician. 1992; 46:1153-67.
Ahmed, Enas M. Hydrogel: Preparation, characterization, and applications: A review, Journal of Advanced Research, vol. 6, Issue 2, 2015, pp. 105-121).
Co-pending U.S. Appl. No. 15/349,824, Amendment After Allowance dated Sep. 27, 2018 and Acceptance of Same, 5 pages.
Co-pending European Patent Application No. 16865154.5, Communication Under Rules 70(2) and 70a(2), Jun. 26, 2019, 1 page.
Co-pending European Patent Application No. 16865154.5, Search Report and Written Opinion, dated Jun. 6, 2019, 9 pages.
Co-pending U.S. Appl. No. 15/653,618, Non-Final Office Action dated Jun. 14, 2019, 9 pages.
Co-pending Australian Patent Application No. 2018205258, filed Jan. 5, 2018.
Co-pending Canadian Patent Application No. 3053451, filed Jan. 5, 2018.
Co-pending Chinese Patent Application No. 201880015144.0, filed Jan. 5, 2018.
Co-pending European Patent Application No. 18736340.3, filed Jan. 5, 2018.
Co-pending Chinese Patent Application No. 201880015144.0, Amendment as filed Jan. 3, 2020 (with english version of the claims).
Co-pending European Patent Application No. 16865154.5, Communication Pursuant to Rule 94(3), dated Feb. 26, 2020, 11 pages.
Co-pending European Patent Application No. 16865154.5, dated Jun. 26, 2019 Communication Under Rules 70(2) and 70a(2), filed Dec. 20, 2019, 18 pages.
Co-pending European Patent Application No. 16865154.5, Voluntary Amendment, filed Dec. 20, 2018, 10 pages.
Co-pending European Patent Application No. 18736340.3, Communication Pursuant to Rules 161 (2) and 162 EPC, dated Aug. 21, 2019, 3 pages.
Co-pending European Patent Application No. 18736340.3, Extended European Search Report and Dpinion, dated Apr. 23, 2020, 15 pages.
Co-pending European Patent Application No. 18736340.3, Response to Aug. 21, 2019 Communication Pursuant to Rules 161(2) and 162 EPC, filed Feb. 28, 2020.
Co-pending U.S. Appl. No. 15/653,618, Final Office Action dated Feb. 12, 2020, 12 pages.
Co-pending U.S. Appl. No. 15/653,618, Response to Jun. 14, 2019 Non-Final Office Action dated Nov. 13, 2019, 11 pages.
Co-pending U.S. Appl. No. 16/156,947, Preliminary Amendment filed Sep. 27, 2019, 10 pages.
Grover, Gregory N. et al. Biocompatible Hydrogels by Oxime Click Chemistry. Biomacromolecules, vol. 13, No. 10, Sep. 12, 2012, pp. 3013-3017. DOI: 10.1021/bm301346e.
Zhang et al. High strength graphene oxide/polyvinyl alcohol composite hydrogels. J. Mater. Chem., 2011, 21, 10388.
Co-pending International Application No. PCT/US19/60986, International Search Report, dated Apr. 2, 2020, 5 pages.
Co-pending National Stage Canadian Patent Application based on PCT/US18/53853, filed Apr. 2, 2020, specification, claims, figues (see WO 2019/070632).

(56) References Cited

OTHER PUBLICATIONS

Co-pending National Stage Chinese Patent Application based on PCT/US18/53853, filed Jun. 2, 2020; specification, claims, figues (see WO2019/070632).
Co-pending U.S. Appl. No. 16/753,302 filed Apr. 2, 2020, specification, claims, figures.

* cited by examiner

Extrusion force of components through dual-barrel injection device

| Injection rate (in/min) | Components | extrusion force (lbf) | Stdev. (lbf) |
|---|---|---|---|
| 6.75 | Component 1 | 7.61 | 1.09 |
| 6.75 | Component 2 | 7.75 | 1.29 |
| 6.75 | Components 1 & 2 | 6.2 | 0.28 |

FIG. 6

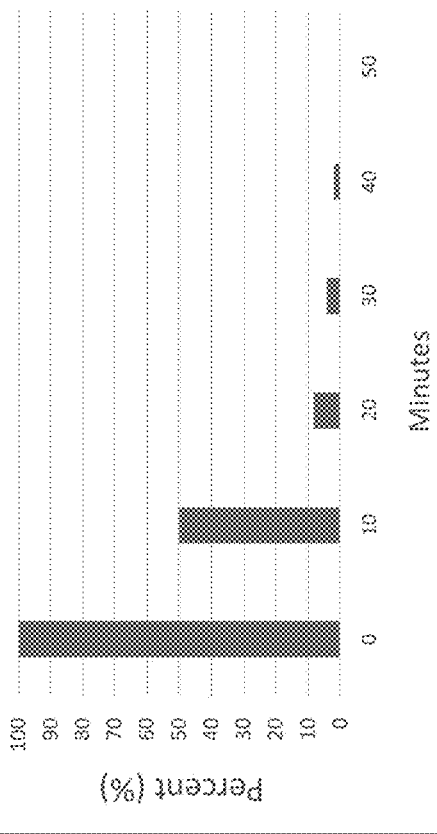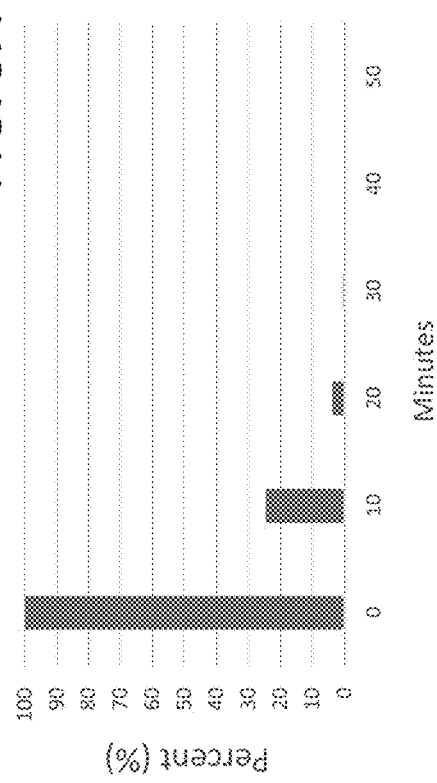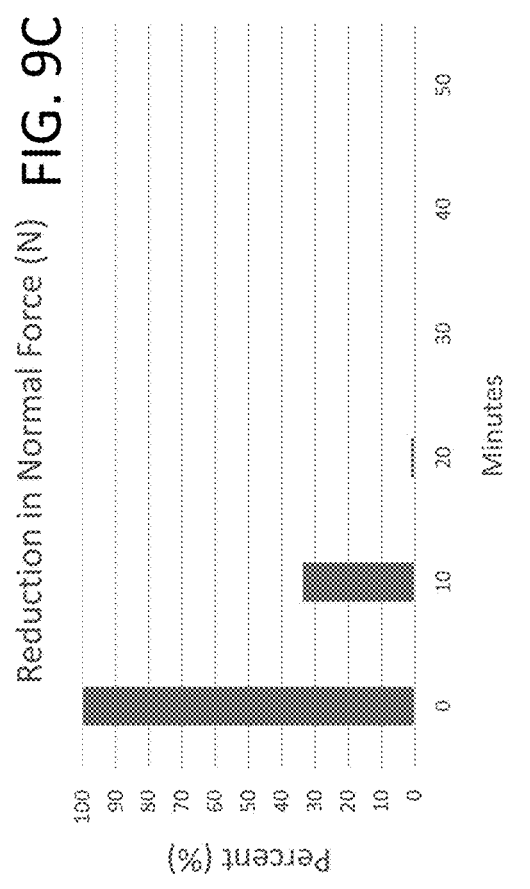

METHODS FOR IMPLANTING AND REVERSING STIMULI-RESPONSIVE IMPLANTS

CROSS-REFERENCE TO RELATED APPLICATIONS

This application relies on the disclosure of and claims priority to and the benefit of the filing date of U.S. Provisional Application No. 62/566,592 filed Oct. 2, 2017 and U.S. Provisional Application No. 62/442,583, filed Jan. 5, 2017. This application is also related to International Application No. PCT/US2016/061671, filed Nov. 11, 2016 and published as WO/2017/083753 on May 18, 2017; U.S. patent application Ser. No. 15/349,806, filed Nov. 11, 2016 and published as U.S. Patent Application Publication No. 20170136144 on May 18, 2017; and U.S. patent application Ser. No. 15/349,824, filed Nov. 11, 2016 and published as U.S. Patent Application Publication No. 20170136143 on May 18, 2017. The disclosures of each of these applications are hereby incorporated by reference in their entireties.

BACKGROUND OF THE INVENTION

Field of the Invention

Embodiments of the present invention are directed to the field of occlusive materials and methods of occlusion. More particularly, embodiments of the present invention are directed to methods for reversible occlusion by way of degradation as a result of exposure to light or through other stimuli. Further, embodiments of the invention include stimuli-responsive materials which can be useful for reversible contraception, embolization, sealants, tissue fillers, or on-command drug delivery.

Description of Related Art

Except for intra uterine devices (IUDs), the contraceptive field lacks methods that are long-lasting and reversible at a later point in time. In addition, the only contraceptives men have available to them are condoms and vasectomy. Vasectomy is a procedure for producing male contraception which involves severing the vas deferens. Potential complications of vasectomy include bleeding at the site of the surgical procedure, which may cause swelling or bruising; infection at the site of the incision; infection in the scrotum; sperm granuloma; congestive epididymitis; recanalization; and the inability to reverse the vasectomy. Additionally, a portion of patients report pain after the procedure. Possibly the largest deterring factor of vasectomy, besides the surgical nature of the procedure, is the difficulty of reversing the vasectomy. The procedure, known as vasovasostomy, is a three to four hours long, expensive microsurgical procedure in which the patient is under general anesthesia. Further, a vasovasostomy does not guarantee the man restores his fertility due to the presence of anti-sperm antibodies that persist in the body after the vasovasostomy.

Due to these potential complications and difficulty in reversing the procedure, alternative procedures for long-lasting, reversible male contraception have been explored. One strategy that has been the subject of research and development is vas-occlusive contraception, which involves injecting or implanting a substance into the vas deferens lumen to occlude this vessel so that the flow of sperm cells from the epididymis is blocked. Particular examples include RISUG, which involves implantation of styrene maleic anhydride, VASALGEL, as well as polyurethane and silicone implants. However, technical barriers for successfully introducing these procedures into the male contraceptive armamentarium have been documented. All prior attempts of reversing vas-occlusive contraceptives have utilized invasive methods such as injecting a solution into the vas deferens to dislodge, de-precipitate, or dissolve the implant, or physically breaking apart the gel via vibration or electric stimulation. These reversal methods have worked in smaller animals, but have failed in larger animals such as canines and non-human primates. To date, a safe and effective method of vas-occlusion reversal that works cross-species has not been shown. Furthermore, minimally-invasive or non-invasive method for vas-occlusion reversal has not been reported. Similarly, there have been attempts for occlusion of the fallopian tubes for female contraception. In particular, ESSURE was a coil implanted into each fallopian tube, and by inducing fibrosis, it blocked the tubes and prevented fertilization. FEMBLOC, a contraceptive in development, involves implanting a biopolymer into the fallopian tubes; similar to ESSURE, FEMBLOC results in permanent occlusion of the tubes. Given their permanent effects, these methods may serve as alternatives to tubal ligations. However, an easily reversible fallopian occlusion device could serve as an effective and safe alternative to intra uterine devices (IUD's) and would be non-hormonal.

Currently, there are no on-command reversible materials that are FDA-approved. There is a need in the art for materials that can form an occlusion in a body lumen and be reversed through a safe and effective method at a later point in time.

SUMMARY OF THE INVENTION

Embodiments of the invention include methods for reversible occlusion of a body lumen by way of degradation as a result of exposure to one or more stimuli such as light. The methods are particular useful for applications in which it is desirable to temporarily occlude a body lumen, such as for contraception. Further, embodiments of the invention include stimuli-responsive materials which can be useful for reversible embolization, sealants, tissue fillers, contraception, or on-command drug delivery.

Specific aspects of embodiments of the invention include Aspect 1, which is a method comprising (a) administering one or more substance(s) into a body lumen of a subject; and (b) forming a stimuli-responsive polymer mass in the body lumen from the one or more substance(s); (c) wherein the mass is sufficient to occlude the body lumen in a manner that prevents transport of at least one material through the body lumen; and (d) wherein the polymer mass is susceptible to on-command reversal in the body lumen upon exposure to one or more stimuli such that after the reversal is performed, the polymer mass no longer occludes the body lumen.

Aspect 2 is a method of Aspect 1, wherein the stimulus is one or more of ultrasound, x-ray, ultraviolet, visible, near infrared, infrared, thermal, magnetic, electric, heat, vibrations, mechanical, aqueous solutions (neutral, basic, or acidic), organic solvent, aqueous-organic mixture, enzymatic, protein(s), peptide(s), small organic molecules, large organic molecules, nanoparticles, microparticles, quantum dots, carbon-based materials, and/or any combination thereof.

Aspect 3 is a method of any one of the preceding Aspects, wherein the body lumen comprises an artery, vein, capillary, lymphatic vessel, a vas deferens, epididymis, or a fallopian tube; a duct including a bile duct, a hepatic duct, a cystic duct, a pancreatic duct, or a parotid duct; an organ including a uterus, prostate, or any organ of the gastrointestinal tract or circulatory system or respiratory system or nervous system; a subcutaneous space; or an interstitial space.

Aspect 4 is a method of any one of the preceding Aspects, wherein the at least one material is a sperm cell and the body lumen is a vas deferens.

Aspect 5 is a method of any one of the preceding Aspects, wherein the at least one material is an oocyte and the body lumen is a fallopian tube.

Aspect 6 is a method of any one of the preceding Aspects, wherein one or more substance(s) is a polymeric precursor material.

Aspect 7 is a method of any one of the preceding Aspects, wherein the polymeric precursor material comprises natural or synthetic monomers, polymers or copolymers, biocompatible monomers, polymers or copolymers such as, but not limited to: polystyrene, neoprene, polyetherether 10 ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers such as polytetrafluoroethylene (PTFE or TEFLON®), TEFLON® TFE (tetrafluoroethylene), polyethylene terephthalate (PET or PETE), TEFLON® FEP (fluorinated ethylene propylene), TEFLON® PFA (perfluoroalkoxy alkane), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly(DTH-iminocarbonate), poly (bisphenol A iminocarbonate), poly(orthoester) (POE), polycyanoacrylate (PCA), polyphosphazene, polyethyleneoxide (PEO), polyethylene glycol (PEG) or any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly (acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, ethylene vinyl alcohol (EVOH), polyethylene oxide, PLA or PLLA (poly(L-lactide) or poly(L-lactic acid)), poly (D,L-lactic acid), poly(D,L-lactide), polydimethylsiloxane or dimethicone (PDMS), poly(isopropyl acrylate) (PIPA), polyethylene vinyl acetate (PEVA), PEG styrene, polytetrafluoroethylene RFE such as TEFLON® RFE or KRYTOX® RFE, fluorinated polyethylene (FLPE or NALGENE®), methyl palmitate, temperature responsive polymers such as poly(N-isopropylacrylamide) (NIPA), polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone (PLCL), and/or chitosan.

Aspect 8 is a method of any one of the preceding Aspects, wherein the mass is a hydrogel.

Aspect 9 is a method of any one of the preceding Aspects, wherein the substance(s) are injected through a multi-syringe system to form the mass.

Aspect 10 is a method of any one of the preceding Aspects, wherein the substance(s) are injected through a needle or catheter or combination of both.

Aspect 11 is a method of any one of the preceding Aspects, wherein the substance(s) are injected through a needle or catheter or combination.

Aspect 12 is a method of any one of the preceding Aspects, wherein the one or more substance(s) form the polymer mass by way of a bioorthogonal reaction.

Aspect 13 is a method of any one of the preceding Aspects, wherein the one or more substance(s) comprises one or more photolabile moieties.

Aspect 14 is a method of any one of the preceding Aspects, wherein the one or more substance(s) comprises one more photolabile moieties linked together.

Aspect 15 is a method of any one of the preceding Aspects, wherein the photolabile moiety is incorporated into the one or more substance(s) through a linkage to a heteroatom, such as oxygen, sulfur, or nitrogen, as an ether, thioester, ester, or amide or amine.

Aspect 16 is a method of any one of the preceding Aspects, wherein the one or more substance(s) comprise a photolabile moiety chosen from one or more of 2-nitrobenzyl, a-bromo-2-nitrotoluene, 2 nitrobenzyl chloride, 5-methyl-2-nitrobenzyl alcohol, 5-hydroxy-2-nitrobenzyl alcohol, 4,5 dimethoxy-2-nitrobenzyl alcohol, 4,5-dimethoxy-2-nitrobenzyl chloroformate, 4,5-dimethoxy-2-nitrobenzyl bromide, 5-chloro-2-nitrobenzyl alcohol, 5-methyl-2-nitrobenzyl chloride, 4-chloro-2-nitrobenzyl alcohol, 2-nitrobenzyl alcohol, 4-chloro-2-nitrobenzyl chloride, 4-fluoro-2nitrobenzyl bromide, 5-fluoro-2-nitrobenzyl alcohol, and 2-methyl-3-nitrobenzyl alcohol, 2 hydroxy-5-nitrobenzyl alcohol, 2-hydroxy-5-nitrobenzyl bromide, 2-methoxy-5-nitrobenzyl bromide, 2-chloro-5-nitrobenzyl alcohol, 2-fluoro-5-nitrobenzyl alcohol, 2-methyl-3-nitrobenzyl chloride, and 2-acetoxy-5-nitrobenzyl chloride, such as 4-[4-(1-Hydroxyethyl)-2-methoxy-5-nitrophenoxy] butanoic acid, α-carboxy-2-nitrobenzyl (CNB), 1-(2-nitrophenyl)ethyl (NPE), 4,5 dimethoxy-2-nitrobenzyl (DMNB), 1-(4,5-dimethoxy-2-nitrophenyl)ethyl (DMNPE), 5 carboxymethoxy-2-nitrobenzyl (CMNB), nitrophenyl (NP), or any of their derivatives, or the photolabile moiety is derived from one or more of benzoin, phenacyl, coumaryl, arylmethyl, thiopixyl, or arylsulfonamides, such as a 1-o-phenylethyl ester, 1-o-nitrophenylethyl, or any of their derivatives, such as a 1-o-phenylethyl ester with an order of magnitude faster degradation than o-nitrobenzyl ester, or the photolabile moiety is O-o-nitrobenzyl o', o"-diethyl phosphate.

Aspect 17 is a method of any one of the preceding Aspects, wherein the one or more stimuli comprises light.

Aspect 18 is a method of any one of the preceding Aspects, wherein the light is monochromatic, ultraviolet, infrared, or visible light.

Aspect 19 is a method of any one of the preceding Aspects, wherein the light is administered through tissue overlying the body lumen.

Aspect 20 is a method of any one of the preceding Aspects, wherein the light is administered by way of a catheter or needle placed in the body lumen.

Aspect 21 is a method of any one of the preceding Aspects, wherein the needle or catheter comprises multiple lumens, such as two or more lumens, with a second lumen capable of delivering a second stimulus.

Aspect 22 is a method of any one of the preceding Aspects, wherein the light has an energy which ranges from 0.01-40 J/cm², such as from 0.1-7 J/cm², or from 0.2-6 J/cm², or less than 20 J/cm².

Aspect 23 is a method of any one of the preceding Aspects, wherein the light has a wavelength ranging from 200 nm to 2,500 nm, such as from 250 nm to 450 nm, or from 300 nm to 425 nm, or from 330 nm to 420 nm, or from 350 nm to 390 nm, or from 365 nm to 405 nm, or from 330 and 460 nm, or from 370 and 440 nm, or from 405 nm to 500 nm, or from 500 nm to 800 nm, or from 700 nm to 2,500 nm.

Aspect 24 is a method of any one of the preceding Aspects, further comprising applying one or more stimuli to the polymer mass to reverse the polymer mass.

Aspect 25 is a method of any one of the preceding Aspects, wherein one or more stimuli change the chemical structure and/or function of the implant.

Aspect 26 is a method of any one of the preceding Aspects, wherein the one or more stimuli comprise a chemical compound which is delivered to the polymer mass and initiates a reverse crosslinking (e.g. Click or bioorthogonal) reaction to depolymerize the polymer mass.

Aspect 27 is a method of any one of the preceding Aspects, wherein the one or more stimuli comprise an enzyme which catalyzes depolymerization of the polymer mass.

Aspect 28 is a method of any one of the preceding Aspects, wherein reversal of the polymer mass restores the flow of fluid, cells, and/or proteins within the body lumen.

Aspect 29 is a method of any one of the preceding Aspects, further comprising administration of light after administration of the one or more substance(s) to catalyze formation of the polymer mass.

Aspect 30 is a method of any one of the preceding Aspects, further comprising administration of light after formation of the polymer mass to reverse the polymer mass.

Aspect 31 is a method of any one of the preceding Aspects, wherein the administration of light required to catalyze formation of the polymer mass is a different wavelength than the wavelength to reverse the polymer mass.

Aspect 32 is a method comprising administering one or more stimuli to a polymer mass in a body lumen for a time and intensity to cause the polymer mass to deteriorate, break down, degrade, disintegrate, dissolve, destroy, remove, dislodge, de precipitate, liquefy, flush and/or reduce in whole or part, thereby reversing the polymer mass.

Aspect 33 is a method of any one of the preceding Aspects, wherein the one or more stimuli comprise one or more of ultrasound, x ray, ultraviolet, visible, near infrared, infrared, thermal, magnetic, electric, heat, vibrations, mechanical, aqueous solutions (neutral, basic, or acidic), organic solvent, aqueous-organic mixture, enzymatic, protein(s), peptide(s), small organic molecules, large organic molecules, nanoparticles, microparticles, quantum dots, carbon-based materials, and/or any combination thereof.

Aspect 34 is a method of any one of the preceding Aspects, wherein the body lumen comprises an artery, vein, capillary, lymphatic vessel, a vas deferens, epididymis, or a fallopian tube; a duct including a bile duct, a hepatic duct, a cystic duct, a pancreatic duct, or a parotid duct; an organ including a uterus, prostate, or any organ of the gastrointestinal tract or circulatory system or respiratory system or nervous system; a subcutaneous space; or an interstitial space.

Aspect 35 is a method of any one of the preceding Aspects, wherein the body lumen is a vas deferens.

Aspect 36 is a method of any one of the preceding Aspects, wherein the body lumen is a fallopian tube.

Aspect 37 is a method of any one of the preceding Aspects, wherein a saline flush is performed after administration of the one or more stimulus to assist in removing the occlusion from the body lumen.

Aspect 38 is a method of any one of the preceding Aspects, wherein the polymer mass is capable of degradation within 1-60 minutes of being exposed to the one or more stimuli.

Aspect 39 is a method of any one of the preceding Aspects, wherein the mechanical properties e.g. G' (storage modulus) or G" (loss modulus) of the polymer mass is altered after administration of the one or more stimuli.

Aspect 40 is a method of any one of the preceding Aspects, wherein the viscosity of the polymer mass is altered after administration of the one or more stimuli.

Aspect 41 is a method of any one of the preceding Aspects, wherein the polymer mass swells or shrinks after administration of the one or more stimuli.

Aspect 42 is a method of any one of the preceding Aspects, wherein the porosity or mesh size of the polymer mass is altered after administration of the one or more stimuli.

Aspect 43 is a method of any one of the preceding Aspects, wherein one or more steps of the method are guided by an imaging modality comprising ultrasound, x-ray, fluoroscopy, MRI, or CT, or any combination of these.

Aspect 44 is a method of any one of the preceding Aspects, wherein reversal of the polymer mass is confirmed by an imaging modality comprising ultrasound, x-ray, fluoroscopy, MRI, or CT, or any combination of these.

Aspect 45 is a method of any one of the preceding Aspects, wherein the polymer mass comprises one or more factors and reversal of the polymer mass causes a release of the one or more factors.

Aspect 46 is a method of any one of the preceding Aspects, wherein the factors are chosen from one or more of spermicidal agents, fertility agents, hormones, growth factors, anti-inflammatory drugs, anti-bacterial agents, anti-viral agents, adherent proteins, antibodies, antibody-drug conjugates, contrast agents, imaging agents, therapeutic drugs, antimicrobials, vasodilators, steroids, ionic solutions, proteins, nucleic acids, antibodies, or fragments thereof.

Aspect 47 is a method of any one of the preceding Aspects, wherein the one or more stimuli comprises light.

Aspect 48 is a method of any one of the preceding Aspects, wherein the light is monochromatic, ultraviolet, visible, near infrared, or infrared light.

Aspect 49 is a method of any one of the preceding Aspects, wherein the light is administered through tissue overlying the body lumen.

Aspect 50 is a method of any one of the preceding Aspects, wherein the light is administered by way of a catheter or needle placed in the body lumen.

Aspect 51 is a method of any one of the preceding Aspects, wherein the light has an energy which ranges from 0.01-40 J/cm², including from 0.1-7 J/cm², or from 0.2-6 J/cm², or less than 20 J/cm².

Aspect 52 is a method of any one of the preceding Aspects, wherein the light has a wavelength ranging from 200 nm to 2,500 nm, including from 250 nm to 450 nm, or from 300 nm to 425 nm, or from 330 nm to 420 nm, or from 350 nm to 390 nm, or from 365 nm to 405 nm, or from 330 and 460 nm, or from 370 and 440 nm, or from 405 nm to 500 nm, or from 500 nm to 800 nm, or from 700 nm to 2,500 nm.

Aspect 53 is a method of any one of the preceding Aspects, wherein the one or more substance(s) comprises one or more photolabile moieties.

Aspect 54 is a method of any one of the preceding Aspects, wherein the one or more substance(s) comprises one more photolabile moieties linked together.

Aspect 55 is a method of any one of the preceding Aspects, wherein the one or more photolabile moieties are incorporated into the one or more substance(s) through a linkage to a heteroatom, including an oxygen atom, a sulfur atom, or a nitrogen atom, or as an ether, thioether, ester, amide, or amine.

Aspect 56 is a method of any one of the preceding Aspects, wherein the one or more substance(s) comprise one or more photolabile moieties chosen from one or more of 2-nitrobenzyl, a-bromo-2-nitrotoluene, 2-nitrobenzyl chloride, 5-methyl-2-nitrobenzyl alcohol, 5-hydroxy-2-nitrobenzyl alcohol, 4,5-dimethoxy-2-nitrobenzyl alcohol, 4,5-dimethoxy-2-nitrobenzyl chloroformate, 4,5-dimethoxy-2-nitrobenzyl bromide, 5-chloro-2-nitrobenzyl alcohol, 5-methyl-2-nitrobenzyl chloride, 4-chloro-2-nitrobenzyl alcohol, 2-nitrobenzyl alcohol, 4-chloro-2-nitrobenzyl chloride, 4-fluoro-2nitrobenzyl bromide, 5-fluoro-2-nitrobenzyl alcohol, and 2-methyl-3-nitrobenzyl alcohol, 2-hydroxy-5-nitrobenzyl alcohol, 2-hydroxy-5-nitrobenzyl bromide, 2-methoxy-5-nitrobenzyl bromide, 2-chloro-5-nitrobenzyl alcohol, 2-fluoro-5-nitrobenzyl alcohol, 2-methyl-3-nitrobenzyl chloride, and 2-acetoxy-5-nitrobenzyl chloride, such as 4-[4-(1-hydroxyethyl)-2-methoxy-5-nitrophenoxy] butanoic acid, α-carboxy-2-nitrobenzyl (CNB), 1-(2-nitrophenyl)ethyl (NPE), 4,5-dimethoxy-2-nitrobenzyl (DMNB), 1-(4,5-dimethoxy-2-nitrophenyl)ethyl (DMNPE), 5-carboxymethoxy-2-nitrobenzyl (CMNB), nitrophenyl (NP), or any of their derivatives, or the photolabile moiety is derived from one or more of benzoin, phenacyl, coumaryl, arylmethyl, thiopixyl, or arylsulfonamides, including a 1-o-phenylethyl ester, 1-o-nitrophenylethyl, or any of their derivatives, including a 1-o-phenylethyl ester with an order of magnitude faster degradation than o-nitrobenzyl ester, or the photolabile moiety is O-o-Nitrobenzyl O', O"-diethyl phosphate.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIG. 6 is a table showing the force necessary to inject and form a stimulus-responsive device.

FIGS. 9A-9C are bar graphs showing reduction in G' (storage modulus) (FIG. 9A), reduction in G" (loss modulus) (FIG. 9B), and reduction in N (normal force) (FIG. 9C) for a stimuli-responsive hydrogel upon exposure to ultraviolet light over time (50 minutes).

DETAILED DESCRIPTION OF THE INVENTION

Figure 1:
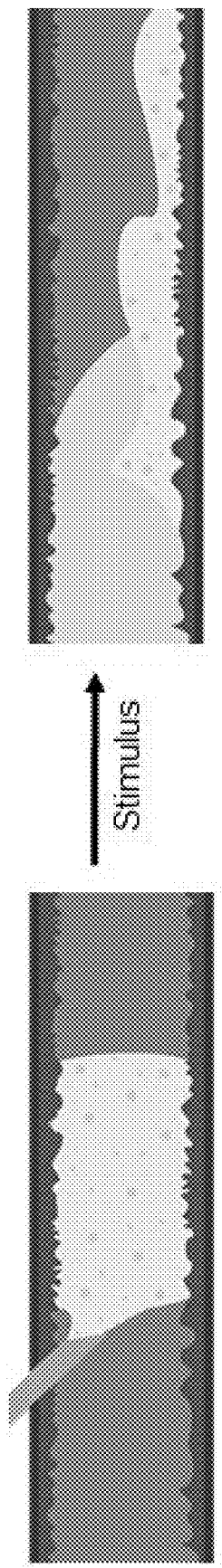
FIG. 1 is a schematic diagram showing an occlusive polymer device that is implanted into a bodily lumen through a needle and then dissolves into an aqueous state upon exposure to a stimulus.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Polymeric Medical Devices and Methods of Reversal

The present invention, in embodiments, describes polymeric medical devices that are formulated in such a way that they are occlusive within a body lumen once implanted, but can be reversed upon command when an external stimulus is applied. Once reversal is performed, the device disintegrates, de-precipitates, dislodges, or dissolves, allowing for the bodily duct to no longer be occluded. Examples of applications where reversible occlusion can be utilized include reproductive tracts such as the vas deferens and fallopian tubes, blood vessels, aneurysms, ducts, tumors, and organs. These reversible polymeric medical devices can also serve as effective sealants such as during surgery or tissue fillers or as wound care dressings or as drug-delivery devices. Examples of reversal can include, but are not limited to, photodegradation (e.g. ultraviolet or infrared exposure), acoustic, and/or enzymatic degradation.

In embodiments, the medical device, such as a polymeric medical device, can be in the form of an implant, hydrogel, gel, mesh, embolization, composition, or device (herein referred to interchangeably as an implant, hydrogel, gel, mesh, embolization, composition, device, occlusive device, occlusive composition, occlusive substance, or any other applicable definition of gel, mesh, composition, device, formulation, or other object or article). In the context of this disclosure, the terms occlusion, occlusive, occlude, occluding and the like refer to the act of occupying space and include but are not limited to blocking, obstructing, disrupting, interfering with, or preventing, in whole or part, movement of a substance from one area to another. In embodiments, the medical device, such as polymer gel, is implanted into the vas deferens or fallopian tubes for male and female contraception, respectively, and can have the function of blocking or otherwise interfering with sperm or the oocyte from traveling within, through or into the relevant tube(s), duct(s), and/or organ(s), thus causing temporary or permanent infertility; preferably, temporary infertility because the gel implantation can be reversed.

In one embodiment, the device is a hydrogel that is injected or implanted into a vessel such as a reproductive organ (e.g. vas deferens, epididymis, uterus, or fallopian tube). The hydrogel is able to occlude or block the flow of cells (e.g. sperm cells or oocyte) resulting in contraception. The pores of the hydrogel are small such that they block the flow of the cells. The hydrogel may also be hydrophilic and swell such that fluid, carbohydrates, proteins (including antibodies), and/or other molecules may be able to travel through. In this manner, the hydrogel is a semi-permeable membrane.

In one embodiment, the hydrogel is formed by having one or more substances cross-link with each other such as macromers. The hydrogel is formed in situ. The hydrogel or its macromers can include components including, but not limited to, a polymer backbone, stimuli-responsive functional group(s), and functional groups that enable cross-linking. The functional groups that enable cross-linking can be end groups on the macromer(s).

The backbone can include one or more of natural or synthetic monomers, polymers or copolymers, biocompatible monomers, polymers or copolymers, polystyrene, neoprene, polyetherether 10 ketone (PEEK), carbon reinforced PEEK, polyphenylene, PEKK, PAEK, polyphenylsulphone, polysulphone, PET, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, TEFLON® TFE, polyethylene terephthalate (PETE), TEFLON® FEP, TEFLON® PFA, and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly-(N-isopropylacrylamine) (PNIPAM), poly(vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly(DTH-iminocarbonate), poly (bisphenol A iminocarbonate), poly(orthoester) (POE), polycyanoacrylate (PCA), polyphosphazene, polyethyleneoxide (PEO), polyethylene glycol (PEG) or any of its derivatives including but not limited to, 4-arm PEG, 8-arm PEG, branched PEG, or linear PEG, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, ethylene vinyl alcohol (EVOH), polyethylene oxide, PLLA, PDMS, PIPA, PEVA, PILA, PEG styrene, Teflon RFE, FLPE, Teflon FEP, methyl palmitate, NIPA, polycarbonate, polyethersulfone, polycaprolactone, polymethyl methacrylate, polyisobutylene, nitrocellulose, medical grade silicone, cellulose acetate, cellulose acetate butyrate, polyacrylonitrile, PLCL, and/or chitosan.

In one embodiment, one or more of the macromers contains a stimuli-responsive functional group. The functional group may be a photolabile moiety. The photolabile moiety may be chosen based on the desired photodegradation method such as ultraviolet (UV), near infrared light (NIR), or infrared light (IR). The photolabile molecule is synthetically incorporated into the macromer through a linkage to a heteroatom such as oxygen, sulfur, or nitrogen or as an ether, thioether, thioester, ester, amide, or amine. Photolabile moieties or groups can include or can be synthesized from compounds including, but not limited to, 2-nitrobenzyl, a-bromo-2-nitrotoluene, 2-nitrobenzyl chloride, 5-methyl-2-nitrobenzyl alcohol, 5-hydroxy-2-nitrobenzyl alcohol, 4,5-dimethoxy-2-nitrobenzyl alcohol, 4,5-dimethoxy-2-nitrobenzyl chloroformate, 4,5-dimethoxy-2-nitrobenzyl bromide, 5-chloro-2-nitrobenzyl alcohol, 5-methyl-2-nitrobenzyl chloride, 4-chloro-2-nitrobenzyl alcohol, 2-nitrobenzyl alcohol, 4-chloro-2-nitrobenzyl chloride, 4-fluoro-2nitrobenzyl bromide, 5-fluoro-2-nitrobenzyl alcohol, and 2-methyl-3-nitrobenzyl alcohol, 2-hydroxy-5-nitrobenzyl alcohol, 2-hydroxy-5-nitrobenzyl bromide, 2-methoxy-5-nitrobenzyl bromide, 2-chloro-5-nitrobenzyl alcohol, 2-fluoro-5-nitrobenzyl alcohol, 2-methyl-3-nitrobenzyl chloride, and 2-acetoxy-5-nitrobenzyl chloride. In one embodiment, the photolabile moiety is 4-[4-(1-Hydroxyethyl)-2-methoxy-5-nitrophenoxy]butanoic acid. The photolabile group can include, but is not limited to, α-carboxy-2-nitrobenzyl (CNB), 1-(2-nitrophenyl)ethyl (NPE), 4,5-dimethoxy-2-nitrobenzyl (DMNB), 1-(4,5-dimethoxy-2-nitrophenyl)ethyl (DMNPE), 5-carboxymethoxy-2-nitrobenzyl (CMNB), nitrophenyl (NP), or any of their derivatives. In another embodiment, the photolabile group is derived from benzoin, phenacyl, coumaryl, arylmethyl, thiopixyl, or arylsulfonamides. In another embodiment, a 1-o-phenylethyl ester, 1-o-nitrophenylethyl, or any of their derivatives, is used as the photolabile moiety. The 1-o-phenylethyl ester has an order of magnitude faster degradation than o-nitrobenzyl ester. O-o-nitrobenzyl O', O''-diethyl phosphate can also be used as the photolabile moiety.

Other examples of photolabile moieties include the nitrobenzyl ether-derived moiety described by A. Kloxin (see A. Kloxin et al., "Photodegradable hydrogels for dynamic tuning of physical and chemical properties", Science. 2009 Apr. 3; 324(5923): 59-63 and U.S. Pat. No. 8,343,710, incorporated by reference in its entirety), as well as those described in U.S. Pat. No. 9,180,196, U.S. Patent Application Publication Nos. US 20160153999 and 20120149781A1, and International Patent Application Publication No. WO2015168090A1, incorporated by reference herein in their entireties.

The structure of the photolabile moiety as well as the atom to which it is linked to affect the efficiency and wavelength required for photodegradation. According to embodiments, the photolabile group is linked to the polymer backbone and/or the end-group through an amide bond. The amide bond prevents hydrolysis from occurring, and thus the device has a longer life span in vivo. According to embodiments, one, both, or all of the macromers contain a stimuli-responsive functional group such as the photolabile moiety. The reversibility is quickest and most efficient when both macromers contain a stimuli-responsive functional group. According to embodiments, one, both, or all of the macromers may contain multiple functional groups such as photolabile moieties linked to each other. In one aspect, the reversibility is quickest and most efficient when multiple functional groups are used.

In one embodiment, the photolabile moiety is chosen based on factors such as its water solubility, decoupling rate, photolysis quantum yield, and the safety of its byproducts. For example, α-carboxy-2-nitrobenzyl (CNB) photolabile group has good water solubility, fast decoupling rates in the microsecond range, high photolysis quantum yields (from 0.2-0.4) and biologically inert photolytic byproducts. The absorption maximum of this CNB group is near 260 nm, with photolysis still occurring at wavelengths as high as 360 nm. Therefore, light at wavelengths <360 nm can be used for degradation purposes. Another example of a photolabile moiety is the 1-(2 nitrophenyl) ethyl group. It can be photolyzed at wavelengths of less than 360 nm. Other examples are 1-4,5-dimethoxy-2-nitrophenyl) ethyl (DM-NPE) and 4,5-dimethoxy-2-nitrobenzyl (DMNB) which absorb and are photolyzed at longer wavelengths (maximum occurring at 355 nm). In such cases, rates of degradation can be lower than those obtained with the use of CNB or the 1-(2 nitrophenyl) ethyl group as a photodegradable moiety. In the use of 5-carboxymethoxy-2-nitrobenzyl (CMNB), a light absorbance maximum occurs at 310 nm, while providing high levels of water solubility to the functional group. The nitrophenyl (NP) caging group is available on the caged calcium reagent NP-EGTA (N6802), a photolabile $Ca^{2+}$ chelator that can be used to rapidly deliver a pulse of $Ca^{2+}$ upon illumination with ultraviolet light, with a high photolysis quantum yield of 0.23.

In one embodiment, the macromers contain functional groups that enable crosslinking of the macromers to form the polymeric medical device. These functional groups are the end groups of the macromer(s). The end groups cross link through a bioorthogonal reaction (sometimes referred to as "Click Chemistry"). A bioorthogonal reaction is utilized because it is highly efficient, has a quick gelation rate, occurs under mild conditions, and does not require a catalyst. One example of such reaction is maleimide and thiol. Another type of Click reaction is cycloaddition, which can include a 1,3-dipolar cycloaddition or hetero-Diels-Alder cycloaddition or azide-alkyne cycloaddition. The reaction can be a nucleophilic ring-opening. This includes openings of strained heterocyclic electrophiles including, but not limited to, aziridines, epoxides, cyclic sulfates, aziridinium ions, and episulfonium ions. The reaction can involve carbonyl chemistry of the non-aldol type including, but not limited to, the formation of ureas, thioureas, hydrazones, oxime ethers, amides, and aromatic heterocycles. The reaction can involve carbonyl chemistry of the aldol type. The reaction can also involve forming carbon-carbon multiple bonds, epoxidations, aziridinations, dihydroxylations, sulfenyl halide additions, nitrosyl halide additions, and Michael additions. Another example of bioorthogonal chemistry is nitrone dipole cycloaddition. The Click chemistry can include a norbornene cycloaddition, an oxanobornadiene cycloaddition, a tetrazine ligation, a [4+1] cycloaddition, a tetrazole chemistry, or a quadricyclane ligation. Other end-groups include, but are not limited to, acrylic, cymene, amino acids, amine, or acetyl. In one aspect, the end groups may enable a reaction between the polymeric device and the cells lining the tube, duct, tissue, or organ that is being occluded.

In other embodiments, the polymeric device is formed by the successive addition of free-radical building blocks (i.e. radical polymerization). A radical initiator is formed which reacts with a monomer, converting the monomer into another radical, resulting in lengthening or propagation of the polymer chain by successive addition of monomers. Non-limiting examples of polymers formed from radical polymerization include polystyrene, poly(acrylic acid), poly(methacrylic acid), poly(ethyl methacrylate), poly(methyl methacrylate), poly(vinyl acetate), poly(ethyleneterephtalate), polyethylene, polypropylene, polybutadiene, polyacrylonitrile, poly(vinyl chloride), poly(vinylidene chloride), poly(vinyl alcohol), polychloroprene, polyisoprene, vinyl fluoride, vinylidene fluoride, trifluoroethylene, poly(methyl-α-chloroacrylate), poly(methylvinyl ketone), polymethacroleine, polyaurylmethacryate, poly(2-hydroxyethylmethacrylate), poly(fumaronitrile), polychlorotrifluoroethylene, poly(acrylonitrile), polyacroleine, polyacenaphthylene, and branched polyethylene. The process of radical polymerization can be initiated by mechanisms including photolysis, thermal decomposition, redox reactions, and ionizing radiation. Thus, a solution of monomers can be delivered in situ to a body lumen, and polymerization can be initiated by way of a device that delivers a stimulus such as light, heat, ionizing radiation, or reagents that initiate redox reactions, to the monomers in situ to initiate polymerization in the body lumen.

In one embodiment, the polymeric device is formed through photoinitiation. Wavelengths greater than 405 nm can be used to add crosslinks and form the device. The same device that is formed through photoinitiation can be photoreversed as long as different wavelengths are used to form and reverse the device.

In one embodiment, the components (e.g. monomers, macromers, or polymers) that form the device have varied molecular weights, component ratios, concentrations/weight percents of the components in solvent, and composition of the solvent. Varying any, some, or all of these properties can affect the mechanical, chemical, or biological properties of the device. This includes properties such as, but not limited to, dissolution time, gelation rate/time, porosity, biocompatibility, hardness, elasticity, viscosity, swelling, fluid absorbance, melting temperature, degradation rate, density, reversal wavelength, reversal time, reversal dosage, and echogenicity.

In embodiments, the polymer forms or dissolves within seconds, minutes, or hours, such as 1, 10, 20, 30, 50, 60 seconds; 1, 2, 3, 4, 5, 6, 7, 8, 9, 10, 15, 20, 25, 30, 40, 45, 50 or minutes; or 1, 2, 3, 4, 5, 6, 7, 8, 9, or 10 hours or more. The rate of polymerization or depolymerization will depend on various factors such as compositions, component ratios, concentration/weight percentages, solvent composition, and other factors as previously described.

In embodiments, the viscosity of the polymer solution ranges from about 0.10 centipoise to about 100,000 centipoise, or any viscosity in between, including 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100,000 centipoise. In other embodiments, the viscosity of the polymer solution ranges from about 1 to about 1,000 centipoise, or from about 1 to 7 Pa*s, such as from about 1 to 3 Pa*s. In other embodiments, the viscosity of the polymer solution ranges from about 1 to about 100 centipoise. By way of illustrative examples, a solution of about 1 centipoise has the viscosity of water, a solution in the hundreds of centipoise has the viscosity of motor oil, a solution of about 1000 centipoise has the viscosity of glycerin, and a solution of about 50,000 centipoise has the viscosity of ketchup. However, it is preferred that the viscosity of the polymer solution is maintained low enough so that it is not too viscous such that the injection cannot be performed with a syringe and needle. The viscosity of the polymer solution can be manipulated by the varying the polymer and/or solvent chosen, the polymer concentration, polymer molecular weight, crosslinking, or by the addition of additional agents including microbubbles and carbon-based materials i.e. graphene.

In one embodiment, the molecular weight of the components can be varied from around 1 kD to 1,000,000 kD. The molecular weight of the polymer is preferred to be from 10 kD to 80 kD. In one example, a high molecular weight can yield small pores in the device and thus, create an effective occlusion. A high molecular weight can also create a more viscous solution and thus, can be more difficult to inject. In other embodiments, the polymers can have a weight average molecular weight ($M_w$) or number-average molecular weight ($M_n$) ranging from about 1,000 to 1,000,000 Daltons as measured by GPC (gel permeation chromatography) with polystyrene equivalents, mass spectrometry, or other appropriate methods. In embodiments, the number-average molecular weight ($M_n$) or the weight average molecular weight ($M_w$) of polymers of the invention can range from about 1,000 to about 1,000,000 Daltons, such as from about 3,000 to about 60,000 Daltons, or from about 20,000 to about 90,000 Daltons, or from about 150,000 to about 900,000 Daltons, or from about 200,000 to about 750,000 Daltons, or from about 250,000 to about 400,000 Daltons, or from about 300,000 to about 800,000 Daltons, and so on. Further, the degree of polymerization of the polymers in embodiments can range from 1 to 10,000, such as from 50 to 500, or from 500 to 5,000, or from 1,000 to 3,000.

In embodiments, the chain length or degree of polymerization (DP) can have an effect on the properties of the polymers. In the context of this specification, the degree of polymerization is the number of repeating units in the polymer molecule. In embodiments, the polymers include from 2 to about 10,000 repeating units. Preferred are polymers which include from 5 to 10,000 repeating units, such as from 10 to 8,000, or from 15 to 7,000, or from 20 to 6,000, or from 25 to 4,000, or from 30 to 3,000, or from 50 to 1,000, or from 75 to 500, or from 80 to 650, or from 95 to 1,200, or from 250 to 2,000, or from 350 to 2,700, or from 400 to 2,200, or from 90 to 300, or from 100 to 200, or from 40 to 450, or from 35 to 750, or from 60 to 1,500, or from 70 to 2,500, or from 110 to 3,500, or from 150 to 2,700, or from 2,800 to 5,000, and so on.

If two or more components are used to form the polymeric medical device, the ratio of the components can be varied. The ratio can be 1:1, 2:1, 1:2, 3:1, 1:3, and so on. a 1:1 ratio allows for the highest degree of cross-linking to occur. The ratio determines the rate of cross-linking and thus, gelation of the device.

For occlusion or tissue fillers, the size of the needle or catheter can be chosen based on the estimated size of the body lumen from the literature, or determined by imaging the dimensions of the lumen of the subject through ultrasound or other imaging modality. In embodiments, the size of the needle can be between 18 gauge to 34 gauge. In other embodiments, the size of the needle is between 21 gauge and 31 gauge. In other embodiments, the size of the needle is at least 23 gauge, such as between 23 gauge and 29 gauge. In another example, the needle that is used to deliver the injection solution contains bores on the side, which allow for the solution to be excreted around the needle, in addition to the bevel.

For sealant or coating applications, the device may be applied using different extrusion approaches, such as through needles, catheters, nozzles, spray applicators, and/or plastic tips. The applicator may be chosen based on factors such as desired application, tissue surface area, coating thickness, and gelation rate.

In one embodiment, the weight percent, or concentration of the components in solution, is varied from around 1% to around 50% of the component in solvent, such as from 1% to 2%, from 2% to 3%, from 3% to 4%, from 4% to 5%, from 5% to 6%, from 6%, to 7%, from 7%, to 8%, from 8% to 9%, from 9%, to 10%, and so on. In another embodiment, the weight percent of the macromer is from around 2.5% to around 20% in the solvent, including 6% to around 20%, 7% to around 20%, 8% to around 20%, as so on. The weight percent can affect the mechanical and chemical properties of the polymer, such as increasing or decreasing pore size, viscosity, hardness, elasticity, density, and degradation.

The solvent that the component is dissolved in can be aqueous (water-based) or an organic solvent e.g. DMSO, PEG, ethanol. The final composition contains excipients for purposes such as increased solubility. The pH of the composition in solution can be varied from 4 to 9, such as from 4 to 5, 5 to 6, 6 to 7, 7 to 8, and 8 to 9. The pH of the solution can affect the gelation time and stability of the macromer in solution.

In one embodiment, the gelation rate and time of the polymer device varies. Gelation can occur instantaneously, in less than 1 minute, or within 1-10 minutes. In one embodiment, the device swells upon contact with the fluids inside the body. Swelling allows for the device to secure itself or "lock" within the lumen to form a good occlusion. The device can swell greater than 100%, such as 100-200%, 200-300%, 300-400%, and so on. The greater the device swells, the greater the likelihood of the device allowing fluid to travel through, and for hydrostatic pressure to be reduced. Swelling may also allow for the device to properly secure itself within the body lumen.

According to another embodiment, the device includes pores. The pores are homogenous on the surface of the device. The porosity is defined by the properties of the macromers and cross-linking of the macromers. In embodiments, the pore diameter of the formed polymer ranges from 0.001 nm to 3 μm, such as from 0.001 nm to 1 μm. In other embodiments, the pore diameter ranges from 0.01 nm to 100 nm, or from about 1 nm to about 1 μm. In other embodiments, the pore diameter is 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 95, 90, 95, or 100 nm. In other embodiments, the pore diameter is at least the size of an atom (0.5 nm). Specific pore sizes can be targeted to provide an optimum porosity that provides maximum flow of fluid while blocking the flow of sperm cells or ova. In other embodiments, the pores range from 0.1 nm to 2 microns in diameter. In one embodiment, the device is suitable for occlusion of reproductive cells. The pores are less than 3 um to prevent the flow of sperm. The pores allow for fluid to travel through the hydrogel. The mesh size of the device is small enough to block reproductive cells from traversing through.

In embodiments, the length of occlusion produced in a body lumen as a result of administering the occlusive substance ranges from 0.1-5 centimeters in length, including 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0 cm in length.

In one embodiment, the device does not degrade inside the body i.e. it is permanent. In another embodiment, the device degrades in the body via an endogenous stimulus (e.g. hydrolysis). The degradation rate is slow enough that the device remains an effective occlusion inside the body for greater than three months. According to another embodiment, the device degrades upon application of an exogenous stimulus e.g. photodegradation (e.g. ultraviolet or infrared exposure), acoustic, and/or enzymatic degradation.

In one embodiment, a multi-syringe system is used to inject or implant the polymeric device for occlusion. Each syringe can inject a separate macromer. The system can also contain a component that mixes the macromer solutions before implanting into the body and has multiple channels that prevent the macromer components from mixing. The macromers cross-link in situ to form the occlusive device. In another aspect, the cross-linking is complete within the injection device prior to the device being implanted into the body. The injection speed and injection volume can be controlled. The injection device can be single use and disposable, or can be multi-use with a replaceable cartridge container in which the macromer solutions are delivered.

In one embodiment, a needle or catheter or combination of both can be used to implant the device into the body. For example, if implanting into the vas deferens, a needle must first be used to puncture the thick layers of smooth muscle. However, an angiocath or over-the-needle catheter can also be used, which first punctures the vas deferens and then replaces the needle with a catheter. This method can circumvent problems such as the needle puncturing the smooth muscle or extravasating the polymeric material past the lumen. If implanting the device into the fallopian tubes, then a catheter based approach must be used to access the tubes. The gauge of the needle and/or catheter can be chosen based on the maximum diameter of the lumen that is being occluded as well as the viscosity of the solutions being injected. For example, it is recommended that for vas deferens occlusion, a needle with a gauge higher than 24 g is used because the inner diameter of the vas deferens is 0.5 mm such as 25 g, 26 g, 27 g, 28 g, 29 g, and 30 g needles. In other embodiments, the needle is extra extra thin walled (XXTW), extra thin walled (XTW), thin walled (TW), or regular walled (RW). Standard needle sizes are readily available such as at http://www.sigmaaldrich.com/chemistry/stockroom-reagents/learning-center/technical-library/needle-gauge-chart.html.

If the device is used to occlude the vas deferens for male contraception, the procedure can be performed surgically or non-surgically. In the surgical method, the physician uses the traditional vasectomy or no-scalpel vasectomy (NSV) technique. The vas deferens is identified, isolated, and then exteriorized through a small puncture in the scrotal skin. Then, the device is injected or implanted once the needle and/or catheter is inside the vas lumen.

Vas-occlusion can also be performed non-surgically such as through percutaneous injection, which may or may not be image-guided (e.g. ultrasound-guided). For example, once the vas deferens is isolated, an ultrasound probe is placed on or near the vas to guide the percutaneous injection. In some embodiments, the method further includes applying ultrasonic energy and visually identifying the vas-deferens by way of ultrasound imaging prior to, during, or after administering the occlusive substance. In some embodiments, the method further includes applying ultrasonic energy and determining an inner (e.g. lumen) diameter, outer diameter, and length of the vas deferens by way of ultrasound imaging prior to, during, or after administering the occlusive substance. In some embodiments, the method further includes applying ultrasonic energy and identifying the lumen of the vas deferens by way of ultrasound imaging prior to, during, or after administering the occlusive substance. In some embodiments, the method further includes applying ultrasonic energy and visually confirming placement of a needle or catheter or a portion thereof into the lumen of the vas-deferens by way of ultrasound imaging prior to, during, or after administering the occlusive substance. In some embodiments, the method further includes applying ultrasonic energy and visually confirming placement of the occlusive substance in the lumen of the vas deferens by way of ultrasound imaging. In some embodiments, when the occlusive substance is a polymer, the method further includes applying ultrasonic energy and monitoring of polymerization of the echogenic vas-occlusive polymer in real time by way of ultrasound imaging. In some embodiments, the method further includes determining one or more dimensions of an occlusion formed by the administered substance inside the lumen of the vas deferens by way of ultrasound imaging.

In embodiments, ultrasound is used to image the vas-deferens and the vas-occlusive polymer during and after placement inside the vas deferens. Ultrasound based imaging is a painless and convenient diagnostic method that functions by projecting sound waves into the body, and then measuring the refraction, reflection, and absorption properties of the imaged-tissue to assess fine structure. Essentially, the way in which certain structures reflect sound waves allows for the generation of an image of the underlying organs and tissues. For instance, ultrasound imaging works best on mechanically more elastic, sound conducting tissues. Calcifications in the body (such as bone, plaques, and hardened tissues) provide degrees of acoustic impedance that makes it difficult to image structures lying below them.

Ultrasound is an ideal candidate for imaging the tissues in the male reproductive system. First, ultrasound imaging is non-invasive and safe. There is no associated ionizing radiation produced with ultrasound as found in X-Ray, PET, and X-Ray imaging. Second, the male reproductive system, specifically the scrotum, does not contain bone, plaques, or hardened tissues which limit acoustic impedance. Finally, preparing a patient for ultrasound imaging is as simple as shaving the area of interest, cleaning the area of interest, applying an ultrasound-conducting fluid interface gel to the surface of the skin, and applying the ultrasound probe in the correct orientation and position. Therefore, ultrasounds are commonly found in urology clinics and are used primarily for imaging the scrotum and penis.

Various frequencies can be used for imaging the vas deferens and/or gel, including contrast-pulse sequencing mode (7 MHZ), B-Mode imaging (14 MHZ), and frequencies in between. Other possible ultrasound modes that can be used for the inventive methods include 2D mode, fusion, harmonic imaging (THI), color mode or color power angio, CW doppler mode, PW doppler mode, M-Mode, anatomical M-mode (live or frozen image), B-Mode, color tissue doppler, PW tissue doppler, panoramic imaging, 3D/4D imaging, and dual imaging. In some embodiments, the frequencies are between 1 and 20 MHZ, including 1, 2, 3, 4, 5, 6, 7, 8, 9, 10, 11, 12, 13, 14, 15, 16, 17, 18, 19, or 20 MHZ. Additionally, the ultrasound can be delivered at different intensities, such as between 0.1 to 1 $W/cm^2$, including 0.1, 0.2, 0.3, 0.4, 0.5, 0.6, 0.7, 0.8, 0.9, and 1.0 $W/cm^2$. Additionally, the ultrasonic energy can be delivered at a specific power, such as 0 to 20 Watts of energy, including 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 Watts. Additionally, the ultrasonic energy can be delivered in pulsed or continuous mode. The ultrasound can be delivered through an ultrasound unit. The ultrasound unit can be portable. An example of a portable ultrasound unit for scrotal imaging is the LOGIQ V2, manufactured by GE Healthcare (Little Chalfont, United Kingdom). Another example of an ultrasound unit for scrotal imaging is the ClearVue 350 by Philips (Amsterdam, Netherlands).

According to embodiments, various ultrasound probes or transducers are used for ultrasound imaging the vas deferens, including sector (phased array), linear and convex transducers. Ultrasound probes and their selection have been discussed in the literature (see T. L. Szabo et al., "Ultrasound Transducer Selection in Clinical Imaging Practice", Journal of Ultrasound in Medicine, 2013, 32(4):573-582). Ultrasound transducers differ according to their piezoelectric crystal arrangement, physical dimensions, shape, footprint (aperture), and operating frequency. It is within the ability of a skilled artisan (e.g. urologist or ultrasound technician) to choose a transducer with appropriate characteristics to image the area of the vas deferens that has been isolated. A hand-held probe can be chosen for imaging that is small enough to image the vas without interfering with other aspects of the procedure such as administration of the occlusive substance.

Transducers are multi-frequency, meaning the frequency can be switched electronically between a range of frequencies (e.g. abdominal transducers have 2-6 MHz). It is important for the user to select the highest frequency which adequate depth of penetration for the anatomic area of interest. In general, the higher the frequency of the transducer, the greater than axial resolution and better the anatomic representation of the image. However, there is a tradeoff between frequency and depth of penetration. For imaging the testis, because of the close proximity of the organ to the surface of the skin, imaging can be performed with high frequency transducers such as a linear array transducer of 12-18 MHz.

There are many factors that impact the image quality. Parameters and settings can be modified by the user of the ultrasound in order to adjust and manipulate the image including: gain, time-gain compensation, frequency, depth/size, field of view, and cine function. A "good quality image" includes: (1) sufficient and uniform brightness, (2) is sharp and in focus, (3) adequate size, and (4) is oriented and labeled for documentation purposes. Furthermore, selection of a transducer is critical for maximizing image quality. Linear array transducer probes produce a rectangular image whereas a curved array transducer produces a trapezoidal shape. Linear array transducers are most commonly used in urology for imaging the testes and male genitalia. However, a curved array transducer can be helpful in visualizing both testes simultaneously.

In regards to safety, the FDA advises that the mechanical index (MI) and thermal index (TI) are kept below 1.90 and 6 degrees C., respectively.

According to embodiments, the non-surgical isolation of the vas deferens includes use of the "three-finger technique" to isolate the vas deferens close to the scrotal skin. According to other embodiments, the non-surgical isolation of the vas deferens includes use of a vas-fixation clamp to grip the vas deferens through the skin of the scrotum. In some embodiments, a combination of these techniques is used. Once isolated and secured beneath the scrotal skin, an occlusive substance such as a vas-occlusive polymer can be administered into the vas deferens by way of percutaneous injection or controlled intra-vasal infusion.

According to some embodiments, the occlusive substance such as a vas-occlusive polymer is innately echogenic. In some embodiments, the polymer device is echogenic due to the presence of microbubbles present in the polymer solution. In other embodiments, the polymer device is echogenic due to other constituents present in the polymer solution.

Embodiments of the invention additionally provide for the use of ultrasonic imaging to confirm placement of the occlusive substance into the vas deferens lumen, determine location of the occlusion, one or more dimensions of the occlusion such as length and diameter, as well as monitor the long-term stability of the occlusion in the vas deferens. In another embodiment, a saline-microbubble solution may be injected into the body lumen and imaged to determine if the microbubbles are occluded by the polymer device. Thus, this ultrasound could be used to determine if an effective occlusion formed. These same embodiments can apply similarly for occlusion of the fallopian tubes for female contraception. For example, the material to occlude the fallopian tubes can be echogenic and imaged using an ultrasound probe (e.g. transvaginal probe).

When the patient requires or desires reversal of the occlusion, a reversal procedure can be performed. Reversal can be performed using ultrasound, x-ray, infrared, thermal energy, magnetic, chemical, enzymatic, physical, vibrational, electric, mechanical stimuli, and/or light. In one embodiment, reversal of the device is performed by exposing energy from an energy source, such as light, to the area where the device is implanted. Light sources include, but are not limited to, ultraviolet (UV), near infrared (NIR), or infrared (IR) light. If the device includes photodegradable monomer(s) or macromer(s), then the monomer(s) or macromer(s) is cleaved and the device transitions from a solid to liquid state when exposed to light. If the monomer(s) or macromer(s) serve a structural purpose, then the cleavage results in mechanical degradation of the device. The device can be designed to only be degraded at specific wavelengths of light or specific intensities of light or a combination of both.

In one embodiment, the device is exposed to the light externally, in which case the reversal procedure is non-invasive and non-surgical. The device can be exposed to light through a catheter or needle inserted into the body lumen, in which case the procedure can be done surgically, non-surgically, or minimally invasively. Light delivering catheters are known in the art, non-limiting examples of which include those described in U.S. Pat. Nos. 7,252,677 and 7,396,354, which are incorporated herein by reference. Further, the light delivering catheter can be capable of delivering both light and/or a solution having an agent that assists in dissolving the device, flushing the device, etc. The catheter or needle can assist in mechanically disrupting the device. If light is delivered through a fiber optic, then the fiber optic can be sculpted to assist in mechanical or chemical reversal of the device. Thus, embodiments of the present invention include methods in which both light and/or a solution and/or a mechanical action are used to reverse the device.

In one embodiment, exposure of the device to light takes place via an external light source. In such a case, bringing the polymer device and the body lumen directly under the skin layers in a clinical setting prior to exposure can increase the penetration of the appropriate light frequencies to the appropriate depth to have the desired degradation effect on the device. Light can be introduced directly to the body lumen and the device through a catheter or needle. The catheter or needle can be inserted percutaneously under ultrasound-guidance. Ultrasound could also be used to determine if the reversal (e.g. degradation, dissolution, or de-precipitation) was successful. The dissolution of the device can be observed in real-time.

In one embodiment, the light can be exposed above the skin and penetrate the skin such that the photoreversible device is exposed. The light can be ultraviolet (UV) or infrared (IR), although infrared (IR) light is able to penetrate skin deeper than ultraviolet (IR). Photodegradation is most effective when the polymer device is most superficial to the skin.

Photoreversal can be accomplished with UV illumination using a UV laser, UV flashlamp, UV fluorescence microscope, or UV fiber optic. A light-emitting diode (LED), violet diode lasers, or a 2-photon light source can be used.

In one embodiment, the ultraviolet light that is used has a defined wavelength. Various wavelengths can impact the degradation rate of the device. The UV wavelengths can range from 260 nm to 405 nm. In one embodiment, the photolabile moiety is designed to detach from the polymer in micro- to milli-seconds by flash photolysis, resulting in a pulse (concentration jump) of the cleaved product when light is applied. There is a significant reduction in the storage modulus, loss modulus, or normal force of the occlusive device when exposed to light. Thus, the device is no longer able to effectively occlude the site. The structure of the photolabile monomer can be modified to allow attenuation of certain wavelengths of light and modification of absorbance properties. The concentration of the monomer can be modified to control light absorbance based on the molar absorptivity of the photolabile group at the wavelength of interest.

Photodegradation can be accomplished with IR light, including but not limited to, near-infrared, short-wavelength infrared, mid-wavelength infrared, long-wavelength infrared, or far-infrared. The wavelength of the infrared light can range from 700 nanometers to 1100 microns. The frequency of the infrared light can range from 300 GHz to 450 THz.

The occlusive device can contain gold nanorods (GNRs) for inducing a photothermal effect. The occlusive device can contain graphene or any of its derivatives for converting the infrared light into heat with high efficiency. The occlusive device can contain nanocrystals for inducing a photothermal effect. In one embodiment, the occlusive device includes up-converting particles (UCNPs). UCNPs can convert low-energy and deeply penetrating NIR to high-energy radiation, such as UV/visible/NIR spectral range through a phenomenon known as photon upconversion. Monotonic UCNPs can be synthesized in a controlled fashion with lanthanide ($Ln^{3+}$) in the host lattice. Other sensitizers such as trivalent $Yb^+$ and $Nd^{3+}$ ions can be activated by 980 nm and 800 nm light. Once activated, the conversion from NIR to UV light can cleave the photolabile moieties to cause reversal of the device from within.

In one embodiment, reversibility is dependent upon light intensity. The light intensity can range from 0.1-40 mW/cm$^2$. It is preferred that a light intensity of less than 40 J/cm$^2$, such as 5-20 mW/cm$^2$, is used. Light intensity can be flood-based (non-polarized light) or laser (polarized). Polarized laser light can allow for increased degradation with lower light intensity due to tuning of the wavelength to a specific frequency. Furthermore, lowered light intensity can contribute to a lower degree of potentially adverse cellular effects. The light can be collimated, or can be partially shielded with an opaque photomask to create exposure gradients. The photomask can be moved at various rates e.g. 0.5, 1.2, 2.4 mm/min.

In one embodiment, the efficacy of the reversal is dependent upon exposure time of the hydrogel to light. Exposure time can range from 1 second to 3,600 seconds. The exposure time is preferably from 1 second to 1,200 seconds. In embodiments, the amount of time sufficient to degrade a particular occlusion sufficient to reverse the occlusive effect depends on the particular photodegradation protocol that is used, the composition of the occlusive material and its photolabile moieties, and the concentration of the photolabile moieties. The amount of time can range for example from 10 seconds to 1 minute, up to 2 minutes, or up to 3 minutes, or up to 4 minutes, or up to 5 minutes, or up to 6 minutes, or up to 7 minutes, or up to 8 minutes, or up to 9 minutes, or up to 10 minutes. In one embodiment, exposure takes place over the course of one or multiple clinical visits, with each exposure further degrading the implanted material.

In one embodiment, reversal is expedited via the addition of other external stimuli outside of the exposure of light from the UV spectrum. In one case, this can include addition of physical stimuli (e.g. ultrasound vibration, cavitation, physical manipulation, muscular stimulation, piercing of the occlusion with a needle, catheter, fiber optic, drill, etc.) In one case, this can include the addition of a secondary chemical agent that degrades the occlusion via secondary chemical means such as enzymatic cleavage, reversal of the crosslinks, ionic solution, pH-altering solution, or addition of some other cleavage factor.

Release of factors from within the device can occur upon exposure to the stimulus (e.g. ultraviolet or infrared light). These factors can include but are not limited to: spermicidal agents, fertility agents, hormones, growth factors, anti-inflammatory drugs, anti-bacterial agents, anti-viral agents, adherent proteins, contrast agents, imaging agents, therapeutic drugs, antimicrobials, anti-inflammatories, spermicidal agents, vasodilators, steroids, ionic solutions, proteins, nucleic acids, antibodies, or fragments thereof. The factors can be released from the device through sustained-release. The patient can self-activate the release of the factors from the device. The factors can be released during an in-office visit to the physician using similar methods that are used to reverse the device e.g. light.

In some embodiments, the reversal procedure involves one or more modalities such as ultrasound, x-ray, infrared, thermal energy, magnetic, chemical, enzymatic, physical, vibrational, electric, or mechanical stimuli. Ultrasound can also be used to determine the location of the device in the body lumen, guide the stimulus to the location of the device, and/or determine if the reversal was successful (e.g. given that the device is partially, mostly, or completely no longer visible on ultrasound). Further, as described below, ultrasound can be used directly to reverse the polymeric device. Any or all of these modalities can be used to modify the rate and degree of degradation. The use of multiple degradation strategies can allow for an increased rate or increased ease of device dissociation.

According to one particular embodiment, a method of reversing an occlusion is provided. The method includes identifying a vessel of a subject in need of reversal of an occlusion; placing an ultrasound probe on or near the vessel and administering ultrasonic energy to image a lumen portion of the vessel, and optionally under guidance of ultrasound imaging, performing one or more or all of the following steps: identifying the occlusion in the vessel;

percutaneously placing a needle or catheter or portion thereof into the lumen portion of the vessel; administering one or more stimulus into the lumen portion of the vessel toward the occlusion; and/or confirming removal of the occlusion inside the lumen portion as a result of administering the stimulus.

In one embodiment, ultrasound is applied at a particular frequency which causes the microbubbles in the polymeric device to vibrate. At a particular threshold of intensity and/or frequency, the microbubbles can be destroyed, which can cause a local shock wave, resulting in cavitation and lysing of the device. Thus, the use of ultrasound can provide a non-invasive method of reversing the occlusive provided by the device. Accordingly, one embodiment of the invention provides a method of reversal of an occlusive device including applying ultrasonic energy to an occlusion at a frequency and/or intensity that is capable of destroying microbubbles inside the occlusion, thereby lysing and destroying the occlusion.

In one embodiment, a level of ultrasonic energy needed for microbubble cavitation is determined. For example, a detector transducer receives a scattered level of ultrasonic energy, indicative of stable cavitation. Accordingly, a method for in vitro or ex vivo testing of microbubble cavitation is used to determine acoustic pressures necessary for reversal. For example, the gel with microbubbles is precipitated in dialysis tubing or in an excised vas deferens or synthetic vas deferens tissue, and an ultrasound probe is applied at varying frequencies, wherein for each frequency, the amount of gel lost is measured. Once a measurement is recorded which is expected to adequately reverse, de-precipitate, liquefy, dissolve, or flush out the polymer gel, such a frequency can be used to reverse, de-precipitate, liquefy, dissolve, or flush out the polymeric medical device in a subject.

Another embodiment of the invention is a method of reversing an occlusion, including: identifying a vessel of a subject in need of reversal of an occlusion; placing at least one ultrasound probe on or near the vessel and administering ultrasonic energy to image a lumen portion of the vessel, and optionally under guidance of ultrasound imaging, performing one or more or all of the following steps: identifying an occlusion in the vessel; and/or administering focused ultrasonic energy at an intensity or frequency capable of breaking down, deteriorating, degrading, disintegrating, reversing, dissolving, destroying, removing, dislodging, de-precipitating, liquefying, flushing and/or reducing the occlusion in whole or part.

In one embodiment, the polymeric medical device is modified or cross-linked with fusion proteins, amino acid sequences, or peptides (natural or synthetic). The polymer can be modified with polyethylene glycol (PEG), where PEGylation can enhance the biocompatibility of the polymer. The amino acid sequence can be cleaved with an endo- or exo-protease. The amino acid sequence can be a dipeptide or tripeptide. The addition of a protease causes the gel to de-precipitate, liquefy, or dissolve for reversal. The protease can occur naturally in the human body or can be an artificial protease. The amino acid sequence and protease can be chosen from a database. The protease can be papain, bromelain, actinidin, ficin, or zingibain. In one embodiment, the di-amino acid scission site can only be cleaved by a bacterial protease. Preferably, the protease is injected in a solution form into the body lumen to reverse, de-precipitate, liquefy, dissolve, or flush out the polymer device.

According to another embodiment of the invention, a method of reversal of an occlusion of a body lumen, such as a reversal of vas occlusive contraception, is provided. The methods of reversal include non-surgically or surgically isolating the vas deferens and administering a solvent into the vas deferens lumen. In embodiments, the solvent is capable of deteriorating, breaking down, degrading, disintegrating, reversing, dissolving, destroying, removing, dislodging, de-precipitating, liquefying, flushing and/or reducing, in whole or part, an occlusion or mass, such as a vas-occlusive polymer occlusion disposed in the lumen of the vas deferens. In some embodiments, the method includes alternatively or in addition applying ultrasonic energy and visually identifying an echogenic polymer occlusion in the lumen of the vas-deferens by way of ultrasound imaging prior to, during, or after administering the solvent. In some embodiments, the method further includes alternatively or in addition applying ultrasonic energy and visually confirming placement of a needle or catheter or a portion thereof into the lumen of the vas-deferens by way of ultrasound imaging prior to, during, or after administering the solvent. In some embodiments, the method further includes alternatively or in addition applying ultrasonic energy and visually confirming dissolution of the echogenic polymer occlusion disposed in the lumen of the vas deferens by way of ultrasound imaging, for example, during or after administering the solvent. In some embodiments, instead of administering a solvent, ultrasonic energy is applied at an intensity and/or frequency capable of breaking down the occlusion. For example, the ultrasonic energy can be applied at an intensity and/or frequency that are capable of lysing microbubbles present in the occlusion, thereby breaking down the occlusion.

Another embodiment includes a method of removing an occlusion disposed in a body lumen, including: imaging a body lumen and an occlusion disposed therein; and performing one or more or all of the following: applying a stimulus into the body lumen and allowing the stimulus to deteriorate, break down, degrade, disintegrate, reverse, dissolve, destroy, remove, dislodge, de-precipitate, liquefy, flush and/or reduce the occlusion in whole or part; and confirming deterioration of the occlusion by way of the imaging. The imaging can include any modality, including ultrasound, MRI, CT, x-ray, PET, PET-CT, or any combination thereof.

Apparatus for Delivering Stimuli

In embodiments, the present disclosure describes an apparatus that is able to deliver a stimulus or stimuli to change an implant disposed in a body, such as in a vessel lumen, body duct, tissue, interstitial space, or organ. Some of the embodiments described below focus on delivery of electromagnetic radiation (EMR) and the impact of the delivered EMR on implants, however, the ability to deliver other stimuli is included as well.

In embodiments, the implant is a polymeric medical device, and an apparatus delivers a stimulus to change the properties of the implant such that it disintegrates, de-precipitates, dislodges, or dissolves. Examples of reversal mechanisms encompassed by stimuli delivered by the apparatus of the invention can include, but are not limited to, photodegradation (e.g. ultraviolet, visible, monochromatic, or infrared exposure), ultrasound, mechanical, electrical, physical, vibrational, magnetic, pH-based, temperature-based, ionic, reverse crosslinking reactions (e.g. Click or bioorthogonal), and/or enzymatic degradation, and any combination thereof. In embodiments, the stimulus is electromagnetic radiation, energy, sound waves, heat, vibrations, aqueous solutions (neutral, basic, or acidic), organic solvent, aqueous-organic mixture, enzymatic, protein(s), peptide(s), small organic molecules (<500 g/mole), large organic molecules (> or =500 g/mole), nanoparticles, microparticles, quantum dots, carbon-based materials, and/or any combination thereof.

In embodiments, the apparatus, system, and methods of the invention are used to change the properties of the implant within a bodily duct, lumen, vessel, tissue, intra-organ space, or organ. The hydrogel can be used to occlude the reproductive duct(s) of a mammal (e.g. vas deferens or fallopian tube) to cause contraception or sterilization. One result of the change in properties of the implant after exposure to the stimulus is that the implant is no longer able to occlude the duct or vessel. In the case of contraception this change would restore fertility.

In embodiments, the apparatus is used to form an implant, or cure or polymerize a hydrogel. The apparatus can deliver a stimulus to enable formation of the occlusive composition.

In embodiments, the apparatus includes components such as a power source, a user interface, a catheter and/or needle, a fiber-coupled light source, and/or an irrigation system, in a combination operable to remove an implant. In one embodiment, the apparatus includes an assembly which includes, but is not limited to, optical fibers, mechanical holding and mounting hardware, and fused silica capillaries. The assembly can vary with respect to the fiber or capillary type, fiber size (e.g. core, clad, buffer), overall assembly size, termination type (e.g. SMA, ST, shaped), end finish, numerical aperture of fiber, shaped end-tips, insertion loss, fiber anchoring (e.g. epoxy, crimp), a jacket, and bend diameters.

In one embodiment, power is supplied to the apparatus via 60V or 120V AC current. However, embodiments of the device are compatible with other voltages according to the single-phase voltage standard that is used in particular countries or regions. In general, this can be in the range of 100-127 volts or 220-240 volts. A representative list of single-phase voltage standard by country can be found on the internet at the world standards website (see http://www.worldstandards.eu/electricity/plug-voltage-by-country/). In one embodiment, the power is supplied to the device by a removable, rechargeable battery pack. In one embodiment, the device is charged using a charging dock. In one embodiment, the power is tunable.

In one embodiment, the user interface for the apparatus includes a mechanism to advance and retract the stimuli introducing catheter. The user interface can include a dial, switch, or programmable interface that allows for modification of the magnitude of the stimulus introduced. In one embodiment, this includes modification of the EMR intensity, including modification of the intensity, the Boolean state of the signal, the frequency of the pulses of the signal, and/or the modification of the wavelength of the EMR. In another embodiment, the user interface allows for control of a flushing solution, including the Boolean state of the flush, the fluid flow rate of the flush, and/or the type of solution being flushed.

In one embodiment, the hand-held catheterization apparatus includes a miniature camera at the tip of the device such as a fiber optic endoscope or fiberscope. The fiberscope, in conjunction with light emitted from the catheterization device, provides capabilities for visualization of the occlusion in situ on a display of the user interface. In this embodiment, the catheterization device is advanced through the lumen until video on the display confirms that the device has reached the occlusion. Further, the fiberscope can confirm removal of the occlusion after one or more stimuli are provided through the catheterization device.

In another embodiment, the hand-held catheterization apparatus includes a nanobot or other miniaturized tools such as drills, boring devices, rotating blades, lances, vibrating hammers, or any other tool capable of delivering a mechanical stimulus tethered to the end of the device that is capable of physically removing portions of the occlusive device and/or breaking up the occlusion through mechanical stimuli. The device can have one or more tools which can be capable of grinding, sawing, piercing, boring, and/or drilling through the occlusion. The one or more tools can be controllable by way of the user interface.

In one embodiment, the user interface includes a computing device or instrument that includes a processor (CPU), graphics processing unit (GPU), and non-transitory computer readable storage media such as RAM and a conventional hard drive, as well as a display. Other components of the computing device can include a database stored on the non-transitory computer readable storage media. As used in the context of this specification, a non-transitory computer-readable medium (or media) can include any kind of computer memory, including magnetic storage media, optical storage media, nonvolatile memory storage media, and volatile memory. Non-limiting examples of non-transitory computer-readable storage media include floppy disks, magnetic tape, conventional hard disks, CD-ROM, DVD-ROM, BLU-RAY, Flash ROM, memory cards, optical drives, solid state drives, flash drives, erasable programmable read only memory (EPROM), electrically erasable programmable read-only memory (EEPROM), non-volatile ROM, and RAM. The non-transitory computer readable media can include a set of computer-executable instructions, or software for implementing the methods, processes, operations, and algorithms of the invention. The computer-readable instructions can be programmed in any suitable programming language, including JavaScript, C, C#, C++, Java, Python, Perl, Ruby, Swift, Visual Basic, and Objective C.

In one embodiment, the apparatus includes a catheter or needle or combination of both by which external stimuli can be introduced. The external stimulus can be introduced subdermally, percutaneously, or intraluminally, to reverse the implant. The apparatus can include a needle-sheathed catheter or a catheter-sheathed needle. The maximum needle size/gauge is determined by the lumen of the vessel, duct, or organ which will receive the external stimulus and as a result the exact size of catheter, needle, or instrument is not critical so long as it is shaped and sized appropriately for a particular application. The gauged needle and/or catheter can have a diameter ranging for example between 100 um and 5 mm, including 0.1 mm, 0.2 mm, 0.3 mm, 0.4 mm, 0.5 mm, 0.6 mm, 0.7 mm, 0.8 mm, 0.9 mm, 1.0 mm, 1 mm, 2 mm, 3 mm, 4 mm, or 5 mm. The needle diameter is preferably between 0.3 mm to 1 mm. In embodiments, the size of the needle can be from 6 gauge to 34 gauge, such as from 10 gauge to 34 gauge, or from 15 gauge to 32 gauge, or from 20 gauge to 26 gauge, or from 22 gauge to 26 gauge, and so on. In other embodiments, the size of the needle is between 21 gauge and 31 gauge. In other embodiments, the size of the needle is at least 23 gauge, such as between 23 gauge and 29 gauge. In other embodiments, the needle is extra extra thin walled (XXTW), extra thin walled (XTW), thin walled (TW), or regular walled (RW). Standard needle sizes are readily available such as at http://www.sigmaaldrich.com/chemistry/stockroom-reagents/learning-center/technical-library/needle-gauge-chart.html. The needle system is used to introduce a secondary catheter within the lumen of the vessel. The needle or catheter can have a length between 0.1 inch and 15 inches, preferably from 0.5 inch to 10 inches, such as from 0.8 to 5 inches, or from 0.4 to 1 or 2 or 3 inches. The needle can be echogenic, or visible on ultrasound.

The needle or catheter system can include a single lumen. In one embodiment, the needle or catheter remains within the body system during stimulus exposure. In another embodiment, the needle or catheter is removed from the body cavity after being utilized to introduce the stimuli within the body. In one embodiment, the needle or catheter system contains multiple lumen, which can be utilized to introduce multiple stimuli to the implant simultaneously or in a particular sequence. In another embodiment, the needle or catheter acts as a space holder to allow for the introduction of a secondary stimuli-introducing mechanism.

In one embodiment, the needle acts to introduce a multi-lumen catheter to the body system. In one embodiment, such a multi-lumen catheter includes a single tubular system with multiple lumen running parallel to each other. In another embodiment, such a multi-lumen catheter includes a nested series of catheters, in that the sheath and lumen of one tubular structure sits internal to another. Each lumen of catheter can include the same or a separate system for delivering a unique stimulus to the occlusive implantation. For example, each lumen of the multilumen catheter can include a fiber optic system, an irrigation system, a fiber-scope, or a miniature ultrasound probe. For example, the Olympus UM-2R, 12 MHz ultrasound probe, and UM-3R, 20 MHz probe, have an outer diameter of just 2.5 mm (Olympus America Inc., Center Valley, Pa.).

In one embodiment, the stimuli introducing component of the device includes a fiber optic in isolation or in combination with any combination of other stimuli.

In one embodiment, EMR is introduced within the body-system by way of a fiber optic catheter. In such an embodiment, the fiber optic catheter is coupled to an LED or other light source such as a laser that remains external to the body system, contained within the device. The fiber optic catheter is then introduced to the interior of the body system via minimally invasive methods, allowing illumination of an implant.

In one embodiment, the fiber optic is advanced within the body-system by a secondary mechanical system or actuator. The fiber optic catheter can be advanced and retracted by rotary motion, unpowered linear action, or powered rotary or powered linear action. The fiber optic catheter can be advanced and retracted according to commands introduced at the user interface of the device.

In one embodiment, the fiber catheter includes layers of materials with varying light-refracting properties. For example, the interior can include high —OH silica, while the sheathing can include low —OH silica. In embodiments, the silica is doped with materials to raise the refractive index (e.g. with $GeO_2$ or $Al_2O_3$) or to lower it (e.g. with fluorine or $B_2O_3$). (see https://www.rp-photonics.com/silica_fibers.html).

In one embodiment, the light emitting end of the fiber optic has a variety of sculpted tips that create different illumination patterns including, but not limited to, "up" taper, "down" taper, lens (convex), lens (concave), lens (spherical ball), diffuser, side-fire, ring-of-light, and angled end. Various sculpted tip shapes may be found at http://www.molex.com/mx_upload/superfamily/polymicro/pdfs/Optical_Fiber_Tips_and_Their_Applications_Nov_2007.pdf. The fiber sculpted tip can be chosen based on the application and type of implantation that requires exposure. The illumination pattern can have a shape or configuration that can be linear, circular, rectilinear, curvilinear, sideways, or can increase/decrease light divergence. In embodiments, the device is configured to emit circular or arced illumination patterns from 0-360 degrees or any range in between including from 15-90 degrees, 30-180 degrees, 60-120 degrees, 90-240 degrees, 180-300 degrees, 45 to 150 degrees, and so on.

In one embodiment, collimation or coupling components are used to provide a stable platform for coupling light into and out of FC/PC, FC/APC, SMA, LC/PC, SC/PC, and ST/PC terminated fibers. The collimation or coupling component can be fixed or adjustable. The collimation or coupling component directs a laser beam from the end of the fiber while maintaining diffraction-limited performance at the desired wavelength.

In one embodiment, the fiber-coupled LED includes a single LED that is coupled to the optical fiber using the butt-coupling technique. The optical fiber can have a diameter that can be between 1 and 1000 microns, or more preferably between 200 and 500 microns, such as from 1 micron to 750 microns, or from 10 microns to 350 microns, or from 50 microns to 150 microns, or from 100 microns to 480 microns, and so on. The optical fiber can also have a diameter in the millimeter range, such as from 1-10 mm, 1-8 mm, 1-5 mm, 2-4 mm, or 2-3 mm for example for arterial or ductal applications. One of skill in the art will know how to upsize or downsize the instrumentation for a particular application.

In one embodiment, two or more, such as more than two, optical fibers are used. The bundle of optical fibers can be used to increase the light intensity. The bundle of optical fibers can have a total diameter between 1000 microns to 10 mm. For instance, for an artery, the total optical fiber or fiber bundle diameter can be between 1 mm to 2 mm for a penile artery, 3 mm to 4 mm for a coronary artery, 5 mm to 7 mm for a carotid artery, and 6 mm to 8 mm for a femoral artery. Similarly, the total optical fiber bundle diameter can be between 2 mm to 4 mm for a hepatic duct, and 1 mm to 3 mm for a pancreatic duct. Thus, the total optical fiber or fiber bundle diameter can be adjusted according to the particular clinical application (e.g., the target vessel in which one wishes to remove an occlusion). Each fiber optic can be run through a different lumen of the catheter or needle system. The fiber optics can be joined or fused together to run in parallel through a single lumen, or bundles fibers can run in parallel in one or more lumens of a multi-lumen catheter.

The coupling efficiency can be dependent on the core diameter and numerical aperture of the connected fiber. The LED can be mounted to a heat sink. A high-powered LED properly mounted to a heat sink exhibits better thermal management over time than an LED without a heat sink. The LED can emit light in the following colors: red, green, blue, amber, violet, warm white, cool white, ultra-violet. The LED can be mounted to printed circuit boards using surface-mount technology (SMT), also known as a surface-mounted device (SMD).

The LED can be high-power and high-current. The LED can also include a low or high thermal resistant material. For high-power, high-current LEDs, a low thermal resistant material is preferred. The forward voltage (V) of the LED can be from 0 to 5 V, such as from 0 to 1 V, 1 V-2 V, 2 V-3V, 3V-4V, or 4V-5V. The forward current ($I_F$) of the LED can be from 0 to 2,000 mA, such as from 200 to 400 mA, 400 to 600 mA, 600 to 800 mA, 800 to 1,000 mA, 1,000 to 1,200 mA, 1,200 to 1,400 mA, 1,400 to 1,600 mA, 1,600 to 1,800 mA, and 1,800 to 2,000 mA. The modulation frequency of the LED can be in the range of 1000 Hz and 3000 Hz, including 1100 Hz, 1200 Hz, 1300 Hz, 1400 Hz, 1500 Hz, 1600 Hz, 1700 Hz, 1800 Hz, 1900 Hz, 2000 Hz, 2100 Hz, 2200 Hz, 2300 Hz, 2400 Hz, 2500 Hz, 2600 Hz, 2700 Hz, 2800 Hz, 2900 Hz, or within any range encompassing any of these values such as from 1,600 Hz to 2400 Hz, 1400 Hz to 2500 Hz, 1700 Hz to 2300 Hz, 1100 Hz to 1900 Hz, 1400 Hz to 1600 Hz, 2300 Hz to 2600 Hz, and so on. The modulation shape of the LED can be varied as well such as triangle, single, or square.

Light emitting diodes have a divergent light emission, with radiance degrading from the center of the cone of irradiation. Optical fiber exhibits a narrow angle of acceptance, predicted as falling between twelve and twenty degrees to normal. Efficiency of the coupling then can be greatly improved by including a lensing system between the fiber optic and the LED.

In one embodiment, the fiber coupled LED involves a system of lensing to increase the coupling efficiency of the system. Such as system can include a microlens, a larger optical lens, or any combinatorial lensing system to more efficiently target the LEDs radiant energy to the fiber acceptance cone.

In one embodiment, the apparatus emits short wavelength electromagnetic radiation. The wavelength can range from $10^{-6}$ nm (gamma) to 2,500 nm (deep violet). The wavelength can range from 365 nm to 405 nm, or from 405 nm to 1000 nm, or from 200 nm to 2,500 nm, or from 250 nm to 450 nm, or from 300 nm to 425 nm, or from 330 nm to 420 nm, or from 350 nm to 390 nm, or from 365 nm to 405 nm, or from 330 and 460 nm, or from 370 nm to 440 nm, or from 405 nm to 500 nm, or from 500 nm to 800 nm, or from 700 nm to 2,500 nm or from 1000 nm to $10^5$ m. The wavelength emitted can depend on the implantation and the wavelength required for the implantation to be stimulated. For example, the implant can be modified using wavelengths between 300 nm and 500 nm, such as from 300 nm to 450 nm, or from 200 nm to 410 nm, or from 250 nm to 350 nm, or from 320 nm to 380 nm, or from 280 nm to 405 nm, or more preferably, between 365 nm and 405 nm, or at any range recited herein.

In embodiments, the apparatus includes a UV lamp coupled with the optical fiber. The UV lamp can emit light in UV-A, UV-B, or UV-C bands. In other embodiments, the apparatus includes an infrared lamp coupled with the optical fiber. In other embodiments, the apparatus includes a visible lamp or LED coupled with the optical fiber. In other embodiments, the apparatus includes a laser coupled with the optical fiber. The laser can be chosen to emit a wavelength from ultraviolet to visible to infrared. Non-limiting categories of laser sources include solid-state lasers, gas lasers, excimer lasers, dye lasers, and semiconductor lasers. An excimer laser is a non-limiting example of a laser emitting at ultraviolet frequencies, while a $CO_2$ laser is a non-limiting example of a laser emitting at infrared frequencies. The choice of the laser will depend on the particular wavelength of light emitted and its relative absorption by the occlusive device. In one embodiment, the laser is a tunable laser which allows adjustment of the output wavelength. Descriptions of various laser sources are available in the art including Thyagarajan, K., Ghatak, Ajoy, *Lasers: Fundamentals and Applications*, Springer US, 2011, ISBN-13:9781441964410, incorporated by reference herein, as well as The Encyclopedia of Laser Physics and Technology (available online at https://www.rp-photonics.com/encyclopedia.html).

Various other sources of EMR wavelengths are known. For example, for gamma rays, radioactive sources such as $^{192}$Ir, $^{60}$Co or $^{137}$Cs are used. For X-rays, an X-ray source such as an X-ray tube is used in conjunction with a collimator and a filter.

Additionally, the device can include a probe that emits radiofrequency waves or microwaves, which are converted to heat in situ. For example, the device can include a miniature radiofrequency probe. The probe emits radiofrequency radiation which results in both resistive and conductive heating of tissue in contact with the probe. In embodiments of methods of this disclosure, the probe can contact the occlusion itself, which can result in resistive and conductive heating of the occlusion. Alternatively, or in addition, the device can include a miniaturized tip that heats through electrical resistance to provide thermal energy to the occlusion. In embodiments, the needle and/or catheter can provide for cooling. In other embodiments, the miniaturized tip is configured to vibrate at selected frequencies. The occlusion can be chemically formulated such that it dissolves upon heating or vibrational energy.

In one embodiment, the apparatus is capable of introducing a particular energy level of EMR to the implantation. The light intensity can range from 0.1-40 $J/cm^2$ such as from 0.1-1 $J/cm^2$, 1-5 $J/cm^2$, 5-10 $J/cm^2$, 10-15 $J/cm^2$, 15-20 $J/cm^2$, 20-25 $J/cm^2$, 25-30 $J/cm^2$, 30-35 $J/cm^2$, or 35-40 $J/cm^2$. It is preferred that less than 40 $J/cm^2$ of light intensity is used for in vivo applications.

The light intensity can be flood based (non-polarized light) or laser (polarized). Polarized laser light can allow for increased degradation with lower light intensity due to tuning of the wavelength to the specific frequency that interacts with the photolabile groups in the polymers of the implant. Furthermore, lowered light intensity can contribute to a lower degree of potentially adverse cellular effects. The EMR such as UV light can be collimated or can be partially shielded with an opaque photomask to create exposure gradients. The photomask can be moved at various rates including 0.5, 1.2, 2.4 mm/min. Further, the frequency of the light stimulus can be varied. For example, ultraviolet light has frequencies that range from $8\times10^{14}$ Hz to $3\times10^{16}$ Hz. If infrared light is used, the frequency can range from 300 GHz to 450 THz. The light stimulus can also be provided in pulses.

In one embodiment, methods of the invention include introducing the needle or catheter into the lumen of a bodily duct, vessel, tissue, interstitial space, or organ containing the implantation. The vessel can first be punctured using a hypodermic needle and then a single lumen catheter or multi-lumen catheter can be inserted into the area of the implanted device, such as for example into, onto, near, or surrounding the occlusive device or implant. Then, a stimulus such as EMR can be introduced through the catheter or needle. For example, the light-conducting fiber can be introduced through the catheter or needle such that the fiber optic is able to be extended into the lumen of the vessel or cavity containing the implantation and is able to apply light onto the surface of the implantation, the side of the implantation, or is able to penetrate the implantation to apply light from within. The methods can include touching the implantation or not when delivering light. In one embodiment, the needle and/or light-conducting fiber punctures or enters the composition then delivers light, such as delivering 360 degrees of light (around the needle or catheter) within the lumen to treat the composition disposed therein. This is especially useful for implantations that are soft materials, such as hydrogels. The illumination pattern can be varied to treat only part of the occlusive device and/or to administer light/energy from only part of the needle or catheter. For example, the device can include an adjustable sheath or other structure for blocking or insulating the light/energy in a manner such that light/energy can be emitted from the device and/or administered to an occlusive device from 5-180 degrees, or from 10-165 degrees, or from 20-135 degrees, or from 30-110 degrees, or from 45-150 degrees, or from 50-95 degrees, or from 55-85 degrees, or from 75-120 degrees, or from 60-110 degrees, and so on, or any range of amount disclosed herein, around an axis running lengthwise through the needle/catheter.

In one embodiment, the exposure time of the stimulus can be seconds, minutes, or hours, but is preferably from 1 second to 20 minutes. The implantation can be removed, impacted, or reversed by the apparatus within seconds, minutes, or hours. In embodiments, the amount of time sufficient to degrade a particular polymer occlusion will depend on the particular polymer make-up/chemistry, degradation protocol, and stimuli that are used, and can range for example from 10 seconds to 1 minute, up to 2 minutes, or up to 3 minutes, or up to 4 minutes, or up to 5 minutes, or up to 6 minutes, or up to 7 minutes, or up to 8 minutes, or up to 9 minutes, up to 10 minutes, up to 20 minutes, up to 30 minutes, up to 60 minutes, up to 1 hour, up to 2 hours, up to 5 hours, up to 10 hours, or up to 12 hours, or longer. The use of multiple stimuli for degradation can result in shorter exposure times that are effective in degrading the polymer occlusion. In one embodiment, exposure takes place over the course of one or multiple clinical visits, with each exposure further degrading the implanted polymer. The time exposure can also be performed over the course of multiple treatments for the same or varying amounts of time. For example, the stimulus can be applied once or more per selected time period, such as per second, minute, hour, day, week or year. For example, the treatment can be applied for a selected amount of time at a selected interval from the time periods and intervals provided above, or for any amount of time or time period or combination thereof.

In one embodiment, the apparatus can be configured to introduce a fluid that is capable of acting on the implantation. The administered fluid can be capable of changing the charge or pH of the environment which the implantation is situated and/or reverse, dissolve, dislodge, or de-precipitate the implantation or assist in removing the reversed, dislodged, dissolved, or de-precipitated implant from the body. In embodiments, the fluid is capable of deteriorating, breaking down, degrading, disintegrating, reversing, dissolving, destroying, removing, dislodging, de-precipitating, liquefying, flushing and/or reducing, in whole or part, the occlusive implantation.

The fluid can be saline, phosphate-buffered saline, Ringer's solution, or a buffered solution, or any other non-toxic solutions or solvents. The fluid can be pressurized. The fluid can contain various buffering agents including citrate, phosphate, acetate, or carbonate for maintaining the pH of the solution. For example, the solutions can include sodium or potassium bicarbonate for maintaining a basic pH. The solution can have a pH from 8-9, a pH of 7 (neutral), or a pH from 6-7. According to embodiments, the occlusive implantation is sensitive to changes in pH such that acidic and/or basic stimuli result in depolymerization of the implant. Further, the fluid can contain one or more agents (chemical or biological, as described below) to act on the implantation and result in dissolution or depolymerization. In addition, the fluid can be or include various organic solvents such as DMSO, or other organic solvents, that are capable of dissolving the polymer of the occlusive implant.

Included in embodiments of the irrigation system is a fluid source such as an IV bag of saline or another solution, an infusion pump such as a Harvard pump capable of being programmed to deliver the fluid through the catheter at a specific rate, and medical tubing such as polyethylene tubing connected to the irrigation system in the catheter. The infusion pump can be programmed to deliver the solution through the catheter at a constant level or in pulses or bursts that exert physical pressure on the occlusion. However, the infusion pump can also be programmed to limit the volume of fluid so that the vessel, duct, or organ does not rupture during administration.

In one embodiment, the apparatus includes a multi-lumen catheter or needle such that two or more different stimuli can be introduced simultaneously. The stimuli can include, but are not limited to, electromagnetic radiation, chemical agent, biological agent (e.g. an enzyme) mechanical stimulus, or irrigation e.g. saline or another solution. For example, the chemical agent can be one that reverses a polymer synthesized by Click Chemistry (see David A. Fulton, "Synthesis: Click chemistry gets reversible" Nature Chemistry 8, 899-900 (2016)). The chemical agent can also be a reducing agent such as glutathione which breaks the cross-links of the hydrogel. The biological agent can be a protease such as papain, bromelain, actinidin, ficin, or zingibain that reverses the gel by digesting fusion proteins, amino acid sequences, or peptides (natural or synthetic) that are cross-linked to the hydrogel. The chemical or biological agent can be delivered in a solution. The stimuli can be delivered in any combination such that each individual stimulus is delivered through a separate lumen of the catheter.

In one embodiment, the apparatus includes a single hand-held unit, in which all systems and subsystems are contained. In one embodiment, the apparatus includes a hand-held unit in which all systems which come in contact with a patient are disposable. In such an embodiment, disposable components can include but are not limited to the piercing needle, a section of fiber optic catheter, and a threaded connection head. An example of a hand-held unit is the Uro-C Cystoscopic System (see https://www.urosee.com/).

In another embodiment, the apparatus includes a non-consumable part (handle) with a consumable catheter/needle. In another embodiment, the apparatus is completely consumable using a built-in battery. As used herein, "consumable" is intended to mean its commercial sense, i.e. intended to be used and replaced.

In another embodiment, the power supply and a portion of the user interface are contained within a table mounted box. Power can be then transmitted to the handheld portion of the apparatus, which can include a LED light source, further user interface components, and a coupling point to the disposable catheter/fiber head.

In any such embodiment of the apparatus, the apparatus includes a subsystem that allows for the introduction of a fluid flush through the stimuli introducing catheter system. A fluid reservoir can be contained within the device itself, or the system can include a port to allow for the introduction of a fluid flush via a secondary syringe introduction system.

In one embodiment, the apparatus includes a disposable system, with all subsystems being contained in one handheld package.

In one embodiment, the apparatus includes a mechanical system, chemical system, and/or electromagnetic system to remove an implantation. The apparatus can include any number of types of systems or combination of systems to remove an implantation from the body by causing a physical or chemical effect on an implantation.

In embodiments, methods for removal of the implantation are guided by ultrasound. In particular, ultrasound can be used to guide placement of the catheter into the lumen of the vessel containing the occlusion. For example, ultrasound can be used to identify the lumen of the vessel, such as a vas deferens or fallopian tube, as well as image a needle that can be used to introduce a catheter into the vessel. Further, the implantation can be imaged using a medical imaging modality prior to using the apparatus, such as ultrasound, MRI, CT, x-ray, PET, PET-CT, or any combination thereof. The imaging can be used to determine the location, occlusive nature, length of the implant, or a combination thereof.

An additional embodiment of the invention includes a method of reversal of an occlusion including non-surgically or surgically isolating the occluded vessel and administering a solvent or solution in the lumen of the vessel that is capable of dissolving the occlusion. For example, the method of reversal can rely on ultrasonic imaging to determine the location of the occlusion in the vessel. Then, the vessel such as a vas deferens can be isolated. Then, a solvent or solution which is capable of dissolving the occlusion can be administered into the lumen of the vessel. Alternatively, the solvent or solution can be used to "flush out" the occlusion. For example, the solvents can include DMSO and the solutions can include sodium or potassium bicarbonate. The solution can have a pH from 8-9, 7-8, 7 (neutral), or 6-7. As an alternative to bicarbonates, other alkaline solutions can be used. Anywhere from 0.01-20 cc of active agent, such as a solvent or solution, can be injected into the lumen of the vas deferens, such as from about 0.01 cc to 0.02 cc, 0.02 to 0.03 cc, 0.03 cc to 0.04 cc, 0.1 cc to 20 cc, 0.2 cc to 15 cc, 0.05 cc to 10 cc, 0.05 cc to 4 cc, or from 0.15 cc to 3 cc, 0.2 cc to 0.5 cc, 0.5 cc to 8 cc, and so on, or any range or amount based on these values. However, the rate and volume of injections are limited such that the injection force does not rupture the walls of the vessel. The dissolution of the polymer occlusion can then be monitored in real time using ultrasound. Absence of the occlusion and patency of the vessel lumen can be confirmed via ultrasound imaging. Further, in the case of removal of the occlusive device from the vas deferens, removal of the polymer occlusion can be confirmed through sperm counts and motility testing of ejaculates.

The apparatus can be a handheld device with a screen similar to a cystoscope. The handheld device can be configured so that a user can push a button to release or extend the optical fiber. Alternatively, the apparatus can shine light above the skin to degrade the implant, such as an otoscope or dental curing device.

The apparatus of the invention has several applications or industrial uses, including male and female contraception, occlusion of any organ, tissue, duct, etc. and/or reversal thereof; occlusion of artery to cause necrosis of tumor and/or reversal thereof; occlusion of aneurysm and/or reversal thereof; sustained release of factors, proteins, stem cells, drugs, antibodies, fertility boosting reagents, antibiotics, microbubbles, liposomes, or nanoparticles.

EXAMPLES

Example 1: Dissolution of an Occlusive Polymer Hydrogel

FIG. 1 is a representation of an occlusive polymer device that is implanted into a bodily lumen through a needle. The injection forms a sturdy hydrogel that secures itself in the lumen. The hydrogel also contains pores on its surface, which are able to block the flow of certain cells, such as sperm for male contraception, or oocytes for female contraception. When the hydrogel is exposed to a stimulus (in this case, the stimulus is in the form of a solution), the hydrogel dissolves into an aqueous state. Thus, the hydrogel no longer occludes the bodily duct.

Example 2: Reversal of Hydrogel Upon Exposure to Light

Figure 2:
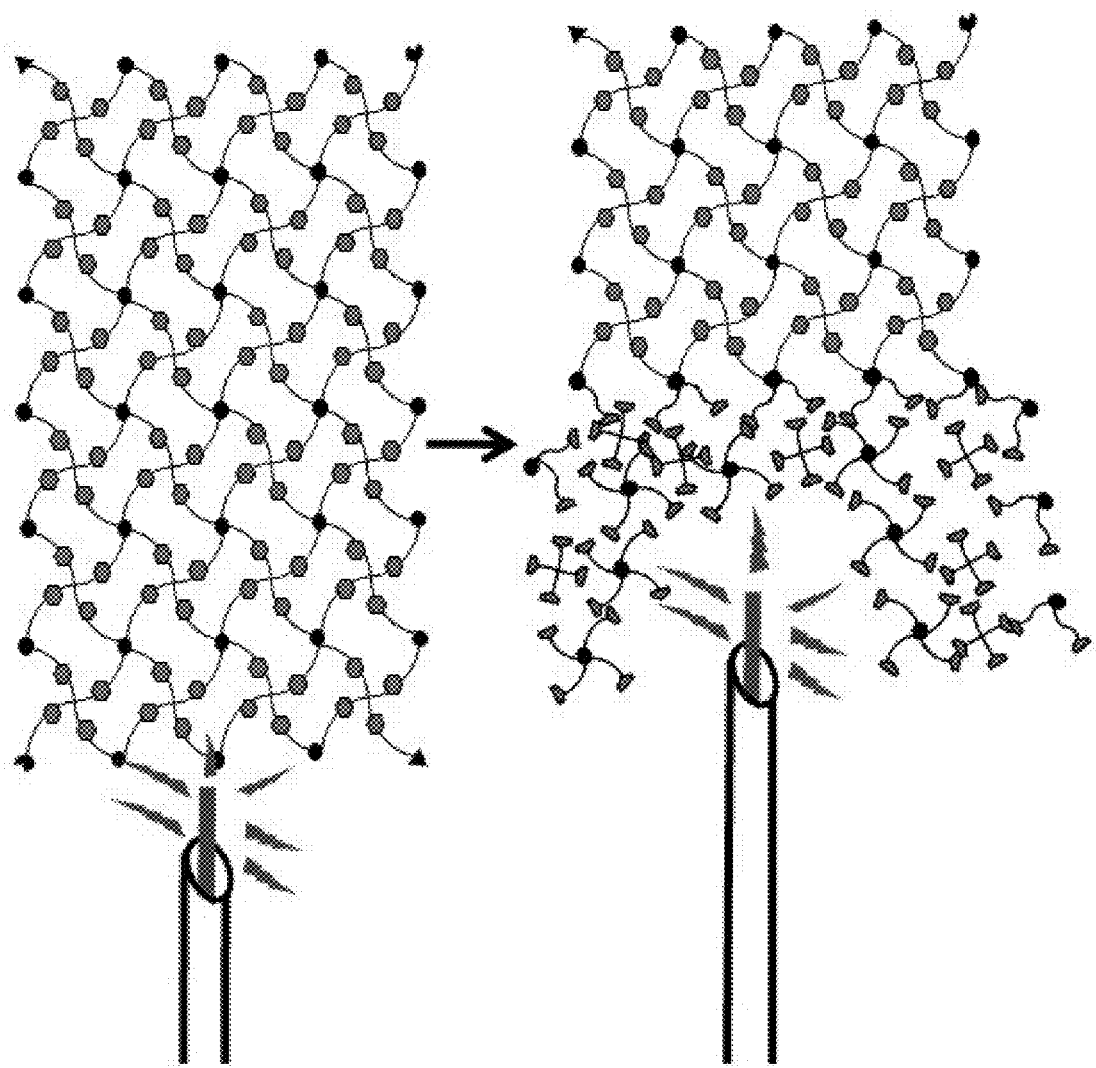
FIG. 2 is a schematic diagram showing a tightly-networked, stimuli-responsive hydrogel being exposed and reversed using light as the stimulus.

FIG. 2 represents a tightly-networked, stimuli-responsive hydrogel being exposed and reversed using light as the stimulus. In this case, the hydrogel is formed from two "star" (4-arm) macromers. Both macromers contain photolabile moieties, which are photocleavable and provide the final hydrogel the ability to be reversed using light. The two macromers form the hydrogel by having their end-groups cross-link through a covalent reaction, such as a bioorthogonal reaction. In the figure, a needle containing a fiber optic is depicted approaching the hydrogel. The fiber optic is emitting light in the visible spectrum, particularly violet. Upon exposure to the light, the photolabile groups within the hydrogel are cleaving and thus, the hydrogel is becoming irreversibly dissolved. Upon cleavage of the tight-network, the hydrogel's mechanical properties become reduced (e.g. storage modulus, loss modulus, normal force).

Example 3: Delivery of Stimulus to a Vas-Occlusive Device

Figure 3:
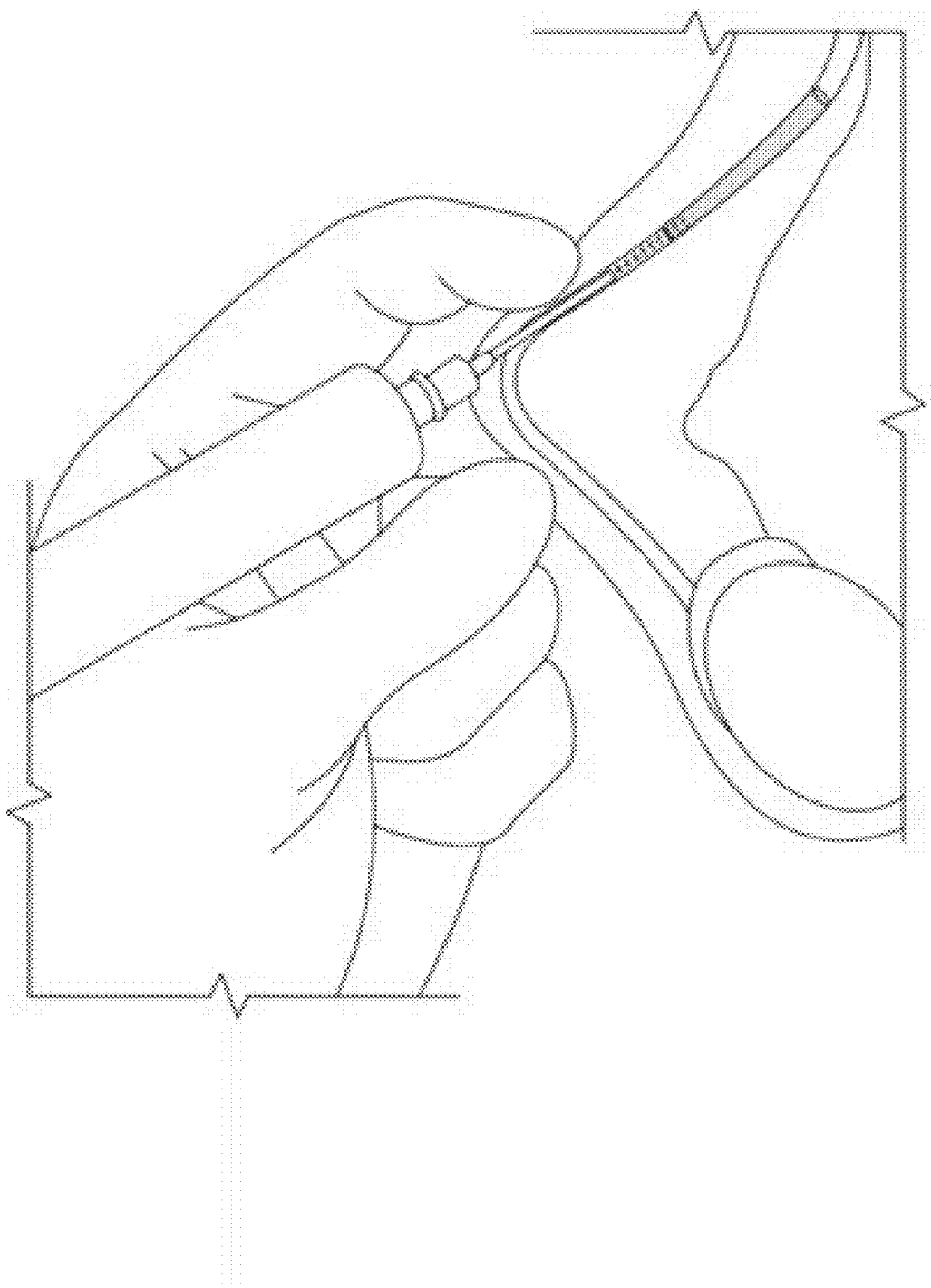
FIG. 3 is a schematic diagram showing delivery of a stimulus to an occlusion in the lumen of the vas deferens according to embodiments of the invention.

FIG. 3 is a schematic diagram showing delivery of a stimulus to an occlusion in the lumen of the vas deferens through a percutaneous method. Ultrasound may also be used to assist in imaging the vas deferens and guiding the percutaneous injection. Alternatively, the vas deferens can be exteriorized through a small puncture in the scrotum, and then the stimulus can be exposed to the occlusion using a needle or over-the-needle catheter.

Example 4: Delivery of Stimulus to Fallopian Tube Occlusion

Figure 4:
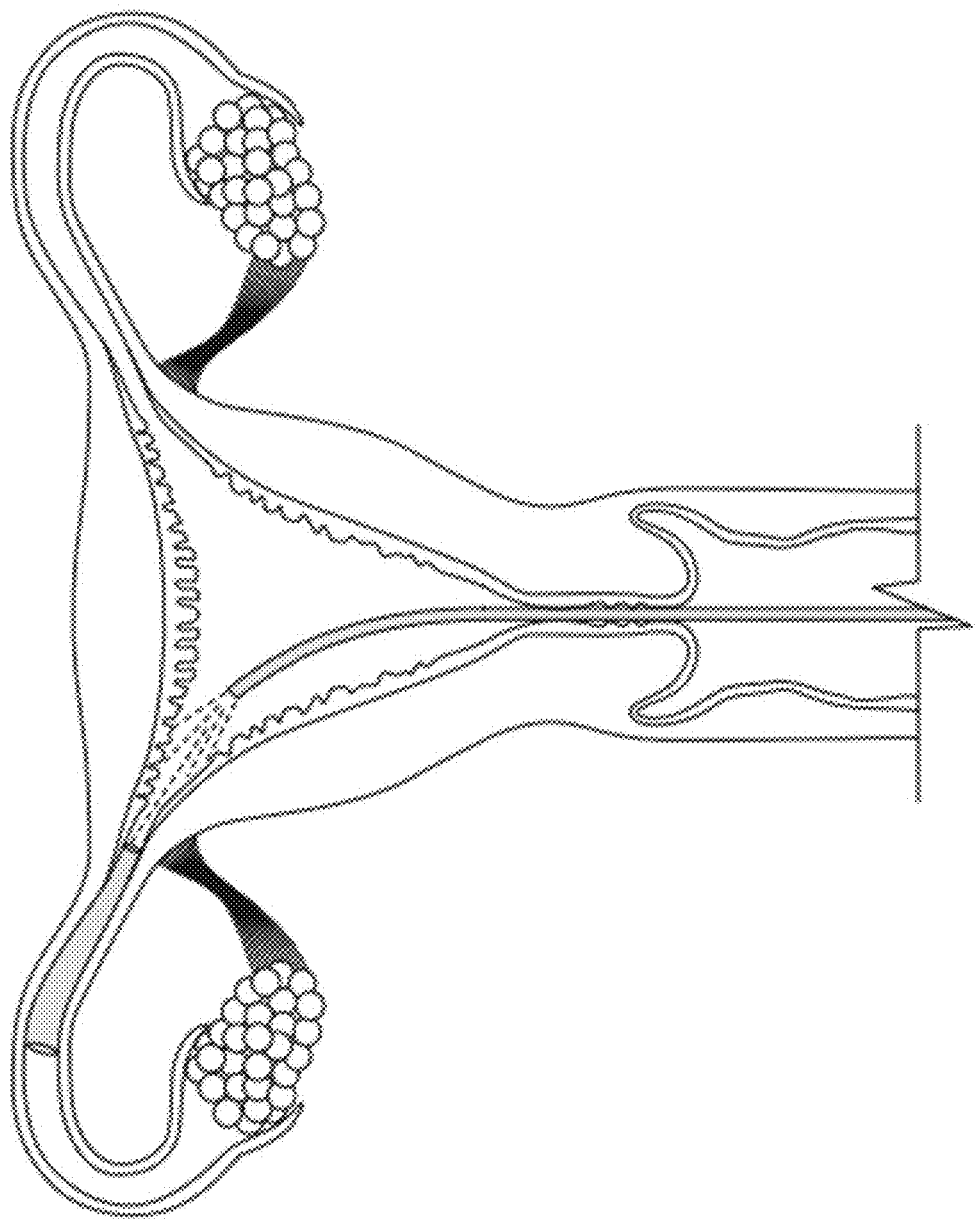
FIG. 4 is a schematic diagram showing delivery of a stimulus to an occlusion in the lumen of a fallopian tube according to embodiments of the invention.

FIG. 4 is a schematic diagram showing an embodiment in which a stimulus is delivered to an occlusion in the lumen of a body, such as an oviduct, through a device of the invention, such as a catheter device. According to embodiments, any stimulus according to those described herein may be delivered. Delivery of the stimulus has an effect on the occlusion to disintegrate, de-precipitate, dislodge, and/or dissolve the occlusion, thereby reversing or otherwise interfering with functionality of the occlusion and the contraception produced by the occlusion.

Example 5: Delivery of Multiple Stimuli Using a Multi-Lumen Catheter

Figure 5:
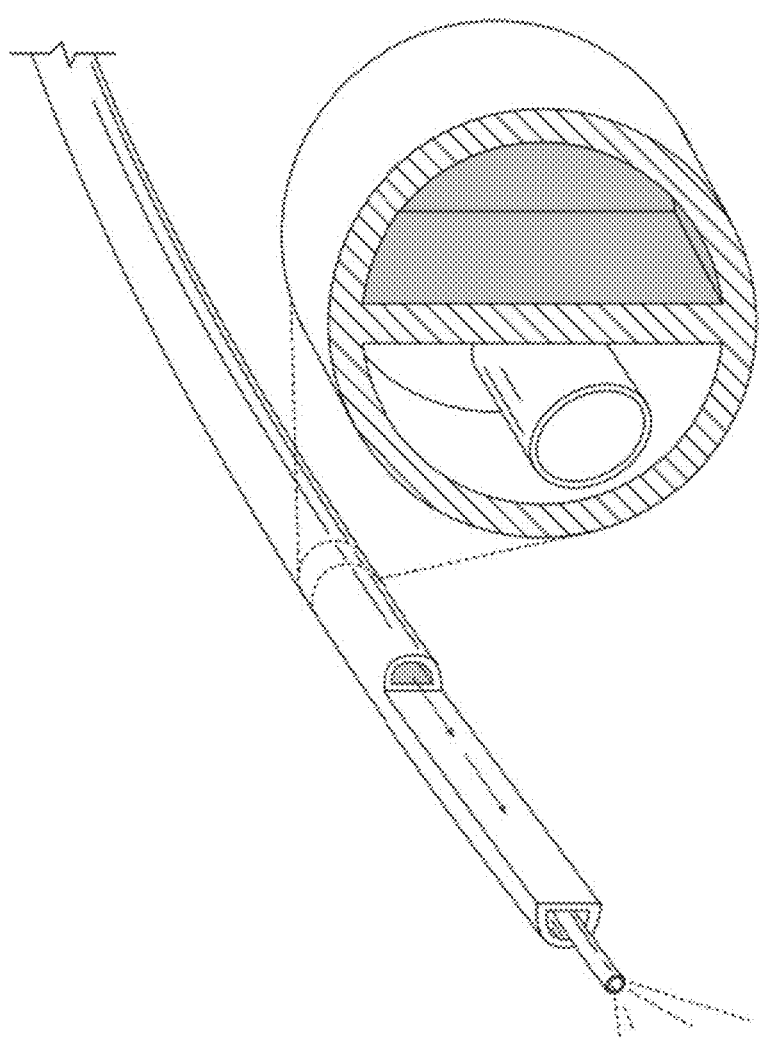
FIG. 5 is a schematic diagram showing a multi-lumen catheter as well as a cross-section of the multi-lumen catheter, which can deliver one or more stimuli to an occlusion in the body lumen according to embodiments of the invention.

FIG. 5 is a schematic diagram showing a catheter device as well as a cross-section of the device. The diagram shows a catheter with multiple lumens, such as two lumens (in this case formed by a wall bisecting the catheter), where one lumen allows passage of a stimulus-delivering device such a fiber optic or bundle of fiber optics and another lumen allows passage or delivery of a fluid stimulus such as an enzymatic solution, pH solution, or saline flush. It is also possible for the lumens of the catheter to deliver fiber optics of different wavelengths. It should be noted that a combination of fiber optics with different wavelengths of light and/or 2 or more solutions may be delivered using the multi-lumen catheter.

Example 6: Injectability of a Stimuli-Responsive Material

The table in FIG. 6 demonstrates the force necessary to inject and form a stimulus-responsive device, as described in this disclosure. Two stimulus-responsive macromers (i.e. components 1 and 2) both containing a PEG-backbone, a photolabile moiety, and cross-link enabling end-groups were synthesized, dissolved in aqueous solutions, and 100 μL of each solution was loaded into respective 1-mL syringes. The syringes were assembled into a dual-barrel injection system. The system allowed for the macromers to mix in a 25 g needle, which is optimal for occluding bodily ducts such as the vas deferens. Next, the dual-barrel injection system was placed into the dynamometer, which pressed on the plungers at a speed of 6.75 in/min. Data collection was stopped when the plungers reached the end of the syringe barrels. The table demonstrates that around 6 lbf was required to inject components 1 and 2 through this system and needle, which is far below the set design criteria (10 lbf).

Example 7: Determining the Device's Mechanical Properties and Mesh Size

Figure 7:
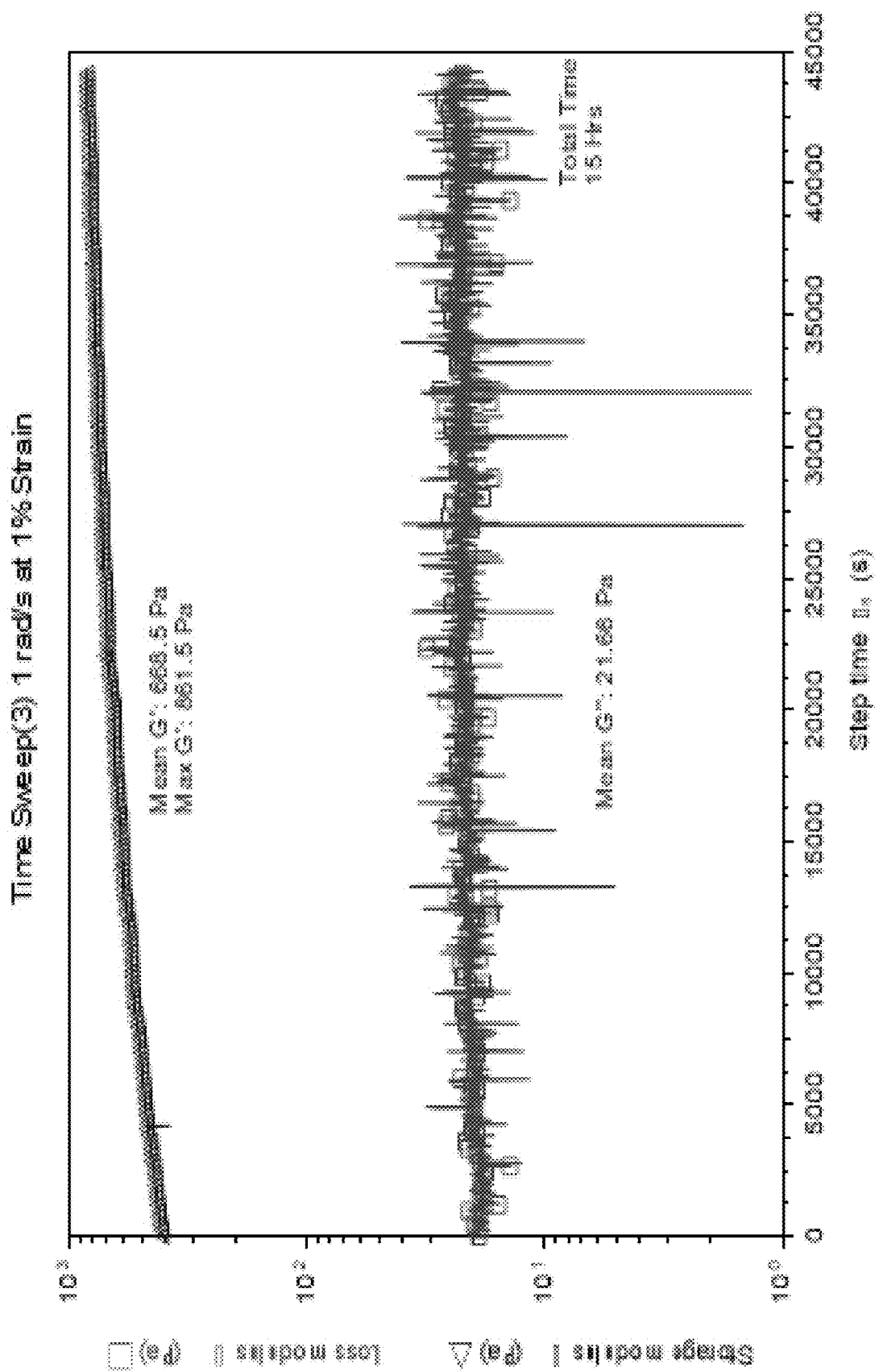
FIG. 7 is graph showing the rheological properties of a stimulus-responsive device formed from two macromers.

The rheological graph in FIG. 7 is a time sweep experiment of an occlusive hydrogel material formed from two macromers, as described in this disclosure. This particular hydrogel formulation has a mean G' (storage modulus) of 668.5 Pa and a mean G" (loss modulus) of 21.66 Pa. The mesh size can be calculated through the following formula:

$$G_p \approx \frac{kT}{\xi^3}$$

From the equation, it is determined that the mesh size for this hydrogel system ranges from 17 to 18.5 nm. Thus, this hydrogel would be an effective occlusion if its purpose was to block reproductive cells; sperm have a diameter of 3-5 um and oocytes have a diameter of 3-8 mm. In comparison, most proteins would be able to traverse through this hydrogel's mesh size (myoglobin=3.5 nm, hemoglobin=5.5 nm; BSA=2 nm; IgG=8 nm; IgM=19 nm).

Example 8: Transformation of a Photolabile Molecule

Figure 8:
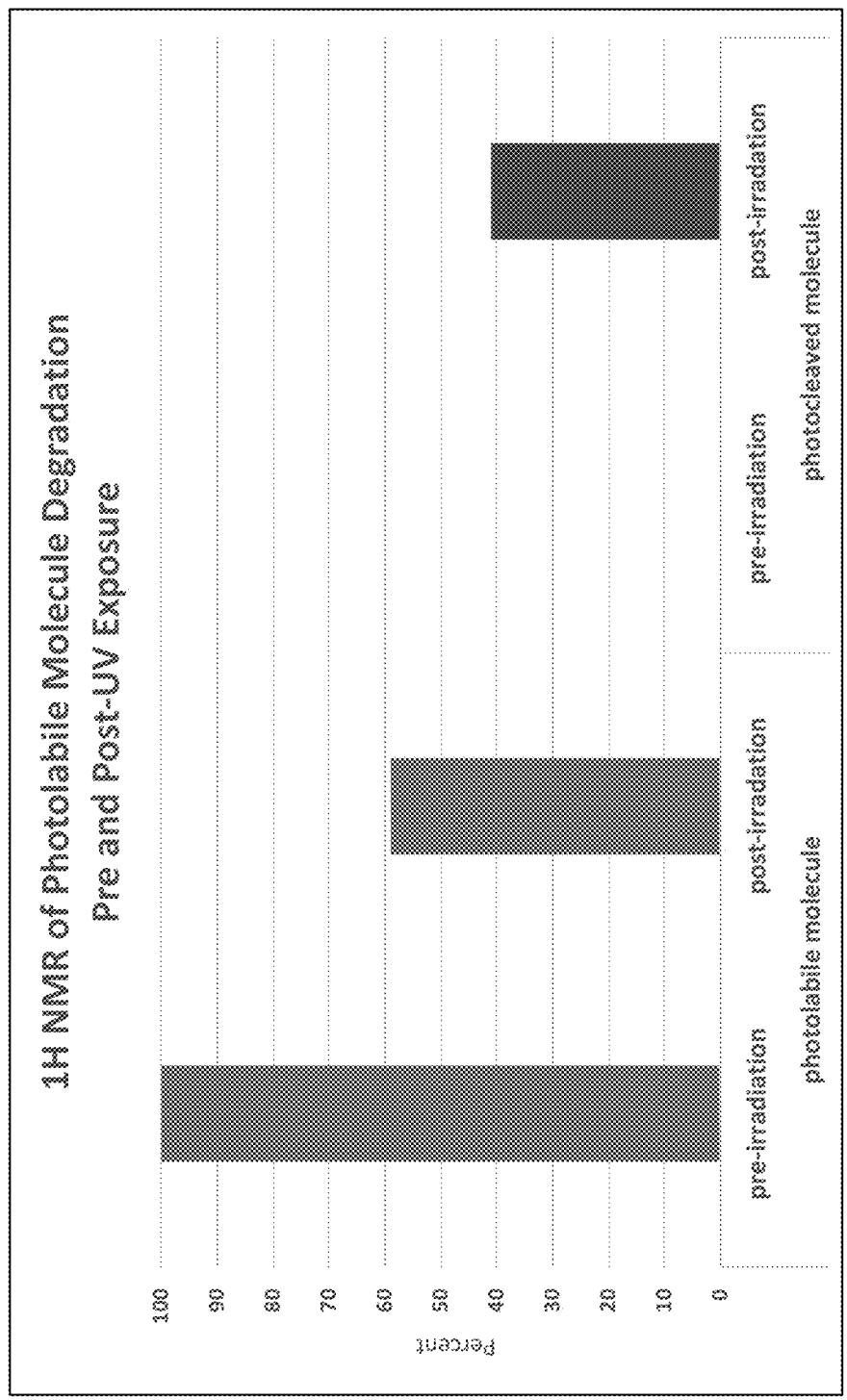
FIG. 8 is a graph of NMR spectra showing degradation of a photolabile moiety, o-nitrobenzyl ester (oNB), as a result of a 2 Joule exposure to light using a fiber optic.

FIG. 8 is a bar graph which shows the chemical transformation of a photolabile molecule (acetylated o-NB) in solution after short exposure to UV-A light using a fiber-optic. The extent of chemical transformation was 41% after the dose applied. FIG. 8 demonstrates that the extent of photoinduced chemical transformation of the photolabile molecule can be tuned based upon dose applied to the system and that this chemical transformation can be monitored by NMR and UV-Vis. The degree of chemical transformation can be varied based on factors including the dose intensity, dose time, as well as wavelength of the light applied. This photolabile molecule or others, as described in this disclosure, may be included in the polymer mass to yield photoreversible properties.

Example 9: Reduction in Mechanical Properties of the Device after Exposure to UV Light The graphs in FIGS. 9A-9C demonstrate: G' (storage modulus) (FIG. 9A), G" (loss modulus) (FIG. 9B), C) N (normal force) (FIG. 9C) for a hydrogel that contains the photolabile molecule described in Example 8 and this disclosure, upon exposure to ultraviolet light over time (50 minutes). As a result of the UV-exposure, the G', G", and N decreased substantially. For example, in the first 10 minutes, the G' decreased by 75.4% and in the first 20 minutes, the G' decreased by 96.2%. After 10 minutes, the gels were dissolved into a liquid state and thus, were reversed.

Example 10: Cytocompatibility of UV Light

Figure 10:
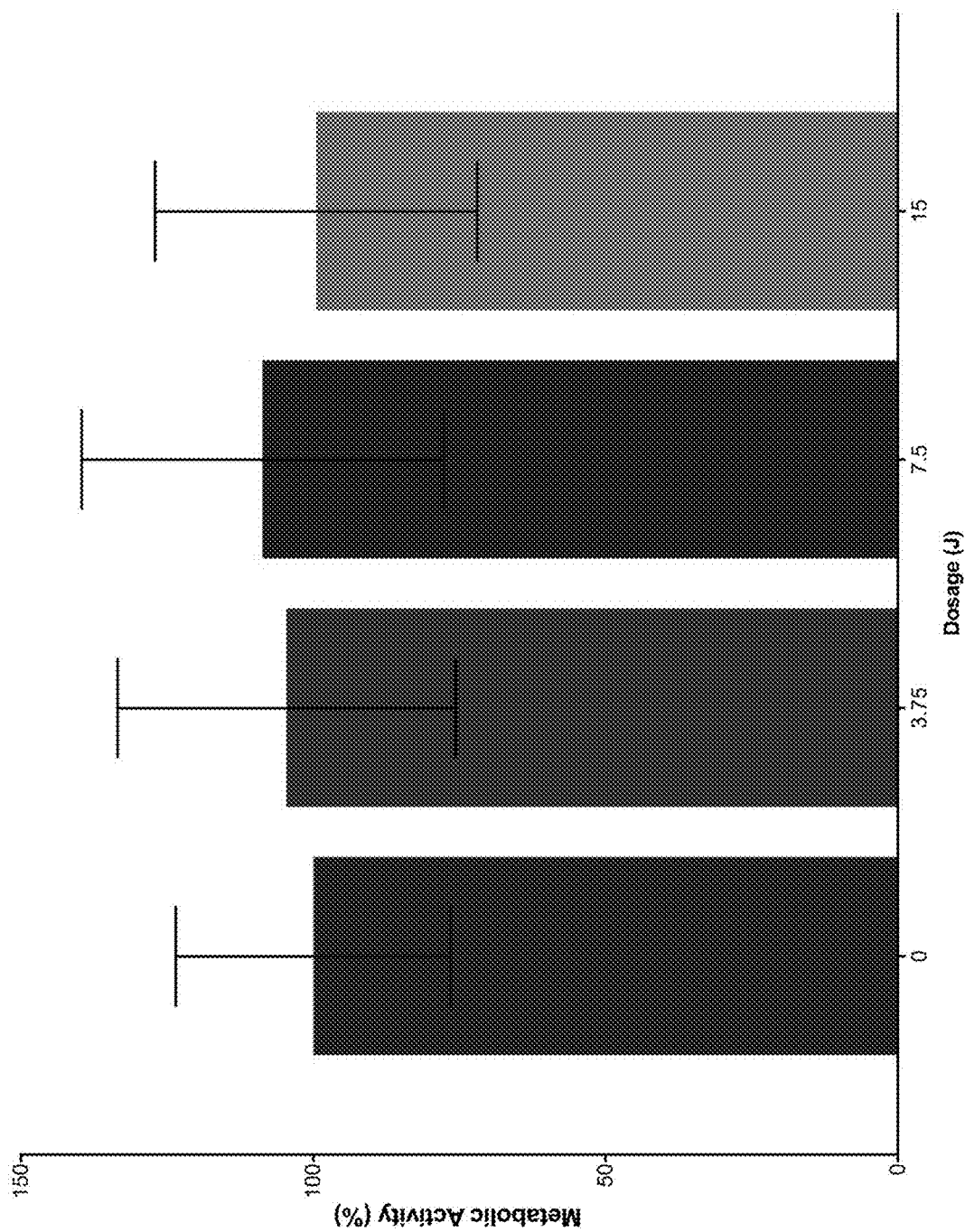
FIG. 10 is a bar graph showing the metabolic activity of Leydig cells after exposure to different dosages of UV light demonstrating the biocompatibility of the UV-exposure on a male reproductive cell line.

FIG. 10 shows the cytocompatibility of a stimulus (in this example, UV-light) as a reversal method. In this experiment, UV-light was exposed directly to Leydig cells, which are found in the testes, and then the metabolic activity of those cells was measured using an Alamar blue assay. There was no statistical difference between the cells not exposed to the stimulus and the cells exposed to 3.75 J, 7.5 J, and 15 J of light.

The present invention has been described with reference to particular embodiments having various features. In light of the disclosure provided above, it will be apparent to those skilled in the art that various modifications and variations can be made in the practice of the present invention without departing from the scope or spirit of the invention. Any apparatus, system or device described herein may be used in any method described herein or any method otherwise available at any time. Likewise, any method described herein can be performed by any apparatus, device, or system described herein or otherwise available at any time. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method comprising:
   administering one or more substance(s) into a body lumen of a subject; and
   forming a stimuli-responsive polymer mass in the body lumen from the one or more substance(s);
   wherein the mass is sufficient to occlude the body lumen in a manner that prevents transport of at least one material through the body lumen;
   wherein the polymer mass is susceptible to reversal in the body lumen upon exposure to one or more exogenous stimuli such that after the reversal is performed, the polymer mass no longer occludes the body lumen;

wherein the mass has the occlusive effect of having pores sized to block the flow of cells within the body lumen and upon exposure to the one or more exogenous stimuli the occlusive effect is reversed to increase the pore size and restore the flow of the cells.

2. The method of claim 1, wherein the one or more exogenous stimuli comprises light.

3. The method of claim 2, wherein the light is monochromatic, ultraviolet, near infrared, infrared, or visible light.

4. The method of claim 2, wherein the light is administered through tissue overlying the body lumen.

5. The method of claim 2, wherein the light is administered by way of a catheter or needle placed in the body lumen.

6. The method of claim 1, wherein the one or more substance(s) are injected through a needle or catheter or a combination of both.

7. The method of claim 6, wherein the needle or catheter comprises multiple lumens.

8. The method of claim 7, wherein the needle or catheter comprises two or more lumens, with a second lumen capable of delivering a second stimulus.

9. The method of claim 1, wherein the one or more exogenous stimuli is one or more of ultrasound, x-ray, ultraviolet, visible, near infrared, infrared, thermal, magnetic, electric, heat, vibrations, mechanical disruption, aqueous solutions, organic solvent, aqueous-organic mixture, enzymatic, protein(s), peptide(s), small organic molecules, large organic molecules, nanoparticles, microparticles, quantum dots, carbon-based materials, and/or any combination thereof.

10. The method of claim 9, wherein the one or more exogenous stimuli is one or more of ultrasound, ultraviolet, visible, near infrared, infrared, magnetic, vibrations, protein(s), peptide(s), small organic molecules, large organic molecules, nanoparticles, microparticles, quantum dots, carbon-based materials, and/or any combination thereof.

11. The method of claim 1, wherein the one or more substance(s) is a polymeric precursor material.

12. The method of claim 11, wherein the polymeric precursor material comprises natural or synthetic monomers, polymers or copolymers, biocompatible monomers, polymers or copolymers, polystyrene, neoprene, polyetherether 10 ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers, polytetrafluoroethylene (PTFE or TEFLON®), TEFLON® TFE (tetrafluoroethylene), polyethylene terephthalate (PET or PETE), TEFLON® FEP (fluorinated ethylene propylene), TEFLON® PFA (perfluoroalkoxy alkane), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly(DTH-iminocarbonate), poly(bisphenol A iminocarbonate), poly(orthoester) (POE), polycyanoacrylate (PCA), polyphosphazene, polyethyleneoxide (PEO), polyethylene glycol (PEG) or any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly (acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, ethylene vinyl alcohol (EVOH), polyethylene oxide, PLA or PLLA (poly(L-lactide) or poly(L-lactic acid)), poly (D,L-lactic acid), poly(D,L-lactide), polydimethylsiloxane or dimethicone (PDMS), poly(isopropyl acrylate) (PIPA), polyethylene vinyl acetate (PEVA), PEG styrene, polytetrafluoroethylene RFE, TEFLON® RFE, KRYTOX® RFE, fluorinated polyethylene (FLPE or NALGENE®), methyl palmitate, temperature responsive polymers, poly(N-isopropylacrylamide) (NIPA), polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly (lactide-co-caprolactone) (PLCL), and/or chitosan.

13. The method of claim 1, wherein the body lumen comprises an artery, vein, capillary, lymphatic vessel, a vas deferens, epididymis, or a fallopian tube; a duct, a bile duct, a hepatic duct, a cystic duct, a pancreatic duct, or a parotid duct; an organ, a uterus, prostate, or any organ of the gastrointestinal tract or circulatory system or respiratory system or nervous system; a subcutaneous space; or an interstitial space.

14. The method of claim 1, wherein the at least one material is a sperm cell and the body lumen is a vas deferens.

15. The method of claim 1, wherein the at least one material is an oocyte and the body lumen is a fallopian tube.

16. The method of claim 1, wherein the administering of one or more of the substance(s) is performed with a needle injected through a wall of the body lumen.

17. The method of claim 1, wherein the stimuli-responsive polymer mass swells greater than 100%.

* * * * *